United States Patent [19]

Crowder, III et al.

[11] 4,384,957
[45] May 24, 1983

[54] MOLECULAR SEPARATION COLUMN AND USE THEREOF

[75] Inventors: Alvin L. Crowder, III, Cromwell; Nils L. Dailey, Wallingford; Joseph V. Fiore, Fairfield, all of Conn.; Kenneth C. Hou, San Antonio, Tex.; Paul J. Marinaccio, Monroe; Eugene A. Ostreicher, Farmington, both of Conn.

[73] Assignee: AMF Incorporated, White Plains, N.Y.

[21] Appl. No.: 287,609

[22] Filed: Jul. 28, 1981

Related U.S. Application Data

[63] Continuation-in-part of Ser. No. 184,822, Sep. 8, 1980, abandoned.

[51] Int. Cl.³ .............................................. B01D 15/08
[52] U.S. Cl. ................... 210/656; 210/198.2; 210/502
[58] Field of Search ..................... 210/198.2, 502, 489, 210/503, 504, 656

[56] References Cited

U.S. PATENT DOCUMENTS

| | | | |
|---|---|---|---|
| 1,197,403 | 9/1916 | Seaver | 210/502 |
| 1,758,412 | 5/1930 | Sheppy | 210/457 |
| 1,764,660 | 6/1930 | Sweetland | 210/489 |
| 2,288,426 | 6/1942 | Stack | 210/489 |
| 2,325,657 | 8/1943 | Burkness | 210/489 X |
| 2,341,414 | 2/1944 | Polivka | 210/502 X |
| 2,798,850 | 7/1957 | Voigtman et al. | 210/502 |
| 3,179,587 | 4/1965 | Battista et al. | 210/502 X |
| 4,263,146 | 4/1981 | Wegmuller et al. | 210/502 |

Primary Examiner—John Adee
Attorney, Agent, or Firm—David E. Dougherty; Michael E. Zall

[57] ABSTRACT

A molecular separation chromotography column for effecting the differential distribution, between two phases, of the components of a sample flowing therethrough. The column contains a substantially homogeneous solid stationary phase which comprises a porous matrix of fiber having particulate immobilized therein, wherein at least one of said fiber or particulate is effective for molecular separation. The column is characterized by a reduced pressure drop, increased axial dispersion, more uniform peak shapes and better separations at high sample loading.

30 Claims, 13 Drawing Figures

MOLECULAR SEPARATION COLUMN AND USE THEREOF

RELATED APPLICATIONS

This is a continuation-in-part of application Ser. No. 184,822 filed Sept. 8, 1980, now abandoned, the entire disclosure of which is incorporated herein by reference.

This application is also related to the following copending application:
U.S. Ser. No. 276,982, filed June 24, 1981 entitled: "Process for Preparing a Zero Standard Serum" to Hou; and
U.S. Ser. No. 238,686, filed Feb. 27, 1981 entitled: "Tissue Culture Medium" to Cone et al, abandoned.
All of these aforementioned copending applications and the contents thereof are not prior art with respect to the invention described and claimed in this application.

BACKGROUND OF THE INVENTION

Numerous techniques exist for the molecular separation of the components of a given sample for either analysis purposes or for product preparation purposes. One type of molecular separation embraces a variety of processes for effecting differential distribution of the sample components between two phases and such processes are generally referred to as chromatography. The differential distribution is achieved by an interchange between a moving phase, which can be a liquid or gas, and a stationary phase.

1. FIELD OF THE INVENTION

This invention relates to novel molecular separation columns, e.g. chromatography columns, and more particularly to a novel stationary phase for use in such columns.

Chromatography is a general term applied to a wide variety of separation techniques based upon the sample interchange between a moving phase, which can be a gas or liquid, and a stationary phase. When gas is the moving phase (or "mobile phase" as referred to in chromatographic terminology), the technique is termed gas chromatography and when liquid is the mobile phase, the technique is termed liquid chromatography.

The so-called "chromatographic adsorption method" of analysis was originated by the Russian botanist, M. Tswett, Ber. Deut. Botan. Ges., 24, 316, 1906, who used it for separating components of plant pigments. Little notice of this work was taken until 1931 and up to 1940 the emphasis was on frontal and displacement analysis. The theory of chromatography was originated by Wilson, J. N., J. Amer. Chem. Soc., 62, 1583, in 1940. Although the important historical role of this work has been largely neglected because the quantitative theory did not allow for diffusion or nonequilibrium between the mobile and the stationary phases, Wilson offered a sound qualitative description of nonequilibrium and its important place in chromatography. He also explained the role of longitudinal diffusion. Although the large spreading effects arising from low adsorption and desorption rates can be diminished by decreasing the flow rates, this in turn gives rise to spreading effects due to large longitudinal diffusion effects.

Following Wilson's work the Nobel prize winning paper of A. J. D. Martin and R. L. M. Synge, Biochem. J., 35, 1358, 1941, appeared which introduced the plate theory of chromatography and revolutionized liquid chromatography. They also suggested using a gas as the mobile phase. Gas chromatography was first tried by A. T. James and A. J. P. Martin, Biochem. J., 50, 6979, in 1952. Since then, however, voluminous literature has been published dealing with gas-liquid and gas-solid chromatography, and gas chromatography has evolved into a sophisticated analytical technique.

Initially, liquid chromatography was performed in large diameter glass columns under normal pressure. These conditions led to long analysis times and a generally tedious procedure. However in recent years, with the introduction of high pressure pumps, advances in both intrumentation and column packings have occurred so rapidly that it has become difficult to keep pace with the amount of literature that is being published, and liquid chromatography is rapidly gaining ground on gas chromatography in becoming of equal stature.

Separations can be classified into either analytical or preparative depending on the objective. In analytical separations, the objective is high resolution separation and identification and quantification of the various components of a sample mixture. In preparative chromatography, on the other hand, the objective is the isolation of pure quantities of the desired constituents in the sample. Liquid chromatography is advantageous over gas chromatography in that the former can be both an excellent analytical as well as a preparative technique. Gas chromatography is very limited in its application as a preparative tool because of the very small sample sizes. In liquid chromatography, on the other hand, milligram to gram quantities of preparative separations are not uncommon depending on the chromatographic column diameter and the amount of stationary phase.

The collection of chromatographic techniques can be classified in several ways and the most fundamental is based on naming the types of phases used. Liquid absorption chromatography is used extensively for organic and biochemical analysis but is limited because there are only a few suitable adsorbents. The distribution coefficient of adsorption often depends on total concentration and this behavior often results in incomplete separations. Gas-solid chromatography has generally suffered from the same defects as liquid adsorption chromatography. Ion exchange chromatography is a special field of liquid-solid chromatography and is specifically applicable to ionic species. Affinity chromatography is based on the attraction (affinity) of a ligand bonded to the solid stationary phase for a given component of the sample. Liquid-liquid or partition chromatography involves the use of a thin layer of liquid held in place on the surface of a porous inert solid as the stationary phase. Paper chromatography is a special field of liquid-liquid chromatography in which the stationary liquid is a film of water adsorbed on a paper mat and thin layer chromatography is similar to paper chromatography except that the paper is replaced by a glass or plastic plate coated with a thin layer of alumina, silica gel or other powdered material.

Column efficiency is generally measured in terms of H, sometimes referred to HETP (height equivalent to a theoretical plate), which is the column length divided by the total number of theoretical plates (n) contained in that length. H is generally considered to be a summation of three contributions, i.e. the contribution from non-equal paths (eddy diffusion), the contribution from diffusion along the column (longitudinal diffusion) and the contribution from non-equilibrium (mass transfer). The eddy diffusion is directly proportional to the diameter of the particles constituting the stationary phase. The less homogeneous the structure, the larger is the contribution from non-equal paths. Conventional chromatographic theory thus predicts that finer packing geometries will have decreased diffusional boundary layers, i.e. shorter paths for material transport to the solid surface which will result in increased efficiency. Current chromatographic theory, and therefore current practice, leads to the use of very fine, homogeneous spherical packing. A complicating factor, however, is that the resistance of the column to fluid flow, i.e. the pressure drop across the column, is inversely proportional to the square of the diameter of the particle. Therefore, halving the particle diameter will increase the pressure drop by a factor of 4.

Additionally, as known in the art, gel substrates are unable to withstand significant pressure drops and/or low flow rates.

2. PRIOR ART

The use of adsorbents or particulates carried by fibers or paper has been used in the filter art for some time, see, for example, the following U.S. Pat. Nos.
  2,143,044 to Wicks et al;
  2,746,608 to Briggs;
  3,238,056 to Pall et al;
  3,253,978 to Bodendorf et al;
  3,591,010 to Pall et al;
  4,007,113 to Ostreicher;
  4,160,056 to Samejima; and
  4,238,334 to Halbfoster.

Carbon has been loaded on a sheet having particles homogeneously distributed and firmly retained therein, as described in U.S. Pat. No. 3,149,023 to Bodendorf et al. The Bodendorf et al sheets are used as cigarette filters, air filters, gas filters, wrappers for fruit and substances prone to discoloration or spoilage by gases in the atmosphere deodorizer layers in laminated sheet products for sanitary napkins, and for surgical dressings for wounds, and the like.

Somewhat similar sheets, as described in the aforementioned patents, have been employed in paper and thin layer chromatography.

Malcolm, U.S. Pat. No. 3,647,684 teaches a thin layer chromatography medium which takes the form of a self-supporting flexible sheet structure having a major proportion of a chromatographic adsorbent such as silicic acid uniformly and homogeneously dispersed with a minor amount of structurally stabilizing inorganic fibers such as glass fibers disposed in a randomly oriented network of a cationic material such as cationic starch.

Leifield, U.S. Pat. No. 3,455,818 teaches sorbent sheets useful for chromatography carried out in the same general manner as conventional thin layer or paper chromatography. The sheets are prepared by dispersing fine fibers of a non-cellulosic material such as fibrous glass together with a high proportion of the desired powdered sorbent in a suitable liquid medium which is flowed onto a porous support followed by removing the liquid. The sheets can be used in a column by rolling one or several of the sheets into a compact roll and inserting it into a glass tube or cylinder such that the interface between sheet surfaces is parallel to and in the path of the mobile phase flow.

Fibers or filament type packings for molecular separation columns have been used, see for example, Miller et al, The Use Of Textile Yarns In Separation Processes, Textile Research Journal, Jan. 1980, pp. 10 et seq.; Brown et al, Macroreticular Resin Columns.I. Model of Bend and Filament Packings, Separation Science and Technology, 15(a), pp. 1533-1553 (1980); and Partridge, Nature, 1123-1125 (March 18, 1967). Other references which suggest the use of fibers for molecular separation packings are:
  U.S. Pat. No. 3,570,673 to Dutzetal;
  U.S. Pat. No. 3,307,333 to Norem et al;
  U.S. Pat. No. 4,169,790 to Pretorius et al; and
  U.S. Pat. No. 4,070,287 to Wiegand.

It is generally accepted in the art that scaling up from laboratory results is difficult, particularly in chromatographic processes where theoretical models are unsatisfactory. The construction of commercial installations based upon knowledge gained from laboratory experiments in this field has turned out to be a major problem. According to those skilled in the art, the use of large columns of resins, for example organic gel columns, is not desirable because of compaction, poor separation results and because of excessive dilution of the eluted components, both of which factors make the process an uneconomical one. If a liquid is introduced evenly across the top of the column, a portion of the front thereof moves downwardly at a rate different from the rate of movement of the balance of the liquid, running obliquely, causing "tailing" and "finger formation" to occur in the bed. To avoid these problems, it is desirable that the front or leading edge of each liquid or eluent, supplied to the top of the column, move downwardly at a uniform rate, the front remaining substantially in a narrow band lying in a horizontal plane.

These prior art problems are discussed, for example, by Baddour in U.S. Pat. No. 3,250,058. Good separations are achieved using thin laboratory columns, but when attempts are made to repeat the separation on a technical or commercial scale, using columns of 5 cm or more in diameter, it is found that "tailing" and "finger formation" occur in the column, both of which causes dilution and poor separation results. Baddour attempts to overcome these problems by the introduction of an arrangement of transverse baffles within the column to induce lateral flow of the liquid flowing through the column. In addition, Baddour finds it necessary to use these baffles in combination with lateral baffles.

The idea of a forced vertical flow in large scale columns was further developed by Lauer et al. in U.S. Pat. No. 3,539,505, who introduced units for radial mixing into the column or divided the column into several short sections as described in German Patent Application DOS No. 2,036,525. Yet another approach to the problem is described in the German patent application DOS No. 2,224,794 and Japanese Pat. No. 73-68752, according to which the column is saturated with the solution which is to be separated. By means of the saturated columns and countercurrent flow, the disturbances caused by density gradients in the column are avoided.

The rather complicated methods which are described above make it possible to conduct large scale chromatographic separation procedures on a commercial basis. However, these methods lead to complicated column structures and to methods which are difficult to accomplish on a commercial scale. Where there are built-in structures within the column, substantial problems occur, for example, when the resin is backwashed. Backwashing is required in these procedures after a certain number of cycles because mechanical impurities from the feed or eluent accumulate on the resin bed so that the performance of the column gradually decreases in efficiency. It is obvious that built-in structures in the column are a nuisance in such situations. The ideas of saturated resin beds and countercurrent flow also lead to complicated structures as described in the German Patent Application DOS No. 2,224,794 or to a complicated procedure of operating the system.

Huber describes another approach in his U.S. Pat. No. 3,856,681 where elongated rod-like elements were arranged parallel to the axis of the column but those elements produced unsymmetrical column cross-sections causing difficult column packing and uneven fluid flow and also limited overall productive output of the column.

Huber, in his U.S. Pat. No. 3,856,681 attempts to obtain uniform flow across a preparative or production chromatography column through the use of a plurality of layers of chromatographic media arranged adjacent to each other, with the thickness dimension of the layers extending substantially perpendicular to the primary fluid flow axis and preferably spaced laterally from each other by relatively inert partitioning means interposed between the layers. If desired, relatively large particles of chromatographic media or relatively inert material can be uniformly distributed through the chromatographic media layer to reduce the overall pressure drop through the final column. The surface of the chromatographic medium is parallel to and in the same direction as the mobile phase fluid flow.

McDonald et al in U.S. Pat. No. 4,211,656 describes a cartridge which triaxially compresses the particulate packing material to assure even flow through the column.

It has now been discovered that a column in which a mobile phase flows through a solid stationary phase can be constructed in direct contradiction to conventional chromatography packing theory if the stationary phase "system" is, broadly, a body of particulate immobilized in a porous matrix of fiber. This new stationary phase has the advantage of both low pressure drop and low diffusion resistance making it particularly suitable for commercial scale separations, particularly liquid separations. Baffle arrangements are unnecessary. As a result, it is possible to construct stable, high flow separation columns of high capacity and shorter run times which have good pressure response, freedom from channeling or fluid bypass, ease of regeneration to reproducible reuse, and the capacity to be shipped under ambient conditions or stored indefinitely. Additionally, the edges of the new stationary phase cooperate with the interior wall of the separation column to form a substantially fluid tight seal therewith, thus preventing channeling near the walls.

SUMMARY OF THE INVENTION

In accordance with the present invention, a molecular separation column is provided for effecting differential distribution, between two phases, of the components of a sample flowing therethrough, said column containing a solid stationary phase which comprises a porous matrix of fiber having particulate immobilized therein, at least one of said fiber or particulate being effective for molecular separation, preferably the particulate, the matrix being substantially homogeneous with respect to each component. When used in liquid-solid flow-through molecular separations, there is a reduced pressure drop and diffusional resistance so that the columns can be used for commercial scale liquid separations in addition to analytical separations.

A method is also provided for effecting molecular separations by the use of such columns as well as providing for a solid phase for use in such columns.

The columns of the present invention, when compared to conventional columns containing similar particulate exhibit lower pressure drops; are less sensitive to high pressures (for example, pressures of 154 kg/cm$^2$ in a 10 mm diameter column do not effect column performance); exhibit more axial dispersion (conventional columns exhibit greater dispersion of the separated components due to mass transfer resistance); exhibit better separation at high sample loadings; are less sensitive to flow rates; and exhibit more uniform peak shapes.

The solid stationary phase of the present invention has advantages in commercial scale chromatographic separations, particularly for high volume, high molecular weight separations. Experiments have shown that the porous matrix provides greater eddy diffusion than particulate alone and at 70% particulate, has a lower diffusional resistance, presumably due to improved flow distribution in the more open matrix. The relatively high eddy diffusion and low diffusion resistance suggest that the porous matrix has two unique features for chromatographic separations—improved separations for components with low diffusion coefficients, and more uniform peak shapes.

Conventional chromatographic theory is quite successful for modeling separations with linear adsorption isotherms. Many separations are apparently linear at low sample concentrations but the separations of commercial interest are often relatively high concentrations and non-linear. The efficiency of the stationary phase of the present invention obtained at high sample concentrations indicates that it is effective for commercial separations.

OBJECTS OF THE INVENTION

An object of the present invention is to provide novel molecular separation solid phase media and columns containing such media.

Another object is to provide novel media which have the characteristics of low pressure drop and low diffusion resistance thereby making it particularly suitable for commercial scale separation, particularly in liquid separations.

A further object is to provide stable, high flow separation columns of good capacity and shorter run times which have good pressure response, freedom from channeling or fluid bypass, ease of regeneration to a reproducible result and the capacity to be shipped under ambient conditions or stored indefinitely.

Yet another object is to provide new solid stationary phase media which cooperates with the interior wall of a separation column to form a substantially fluid-tight seal and thereby prevent channeling near the walls.

These and other objects of the invention will become apparent to those skilled in the art from the following description.

DESCRIPTION OF THE INVENTION

As used throughout this specification, the term "molecular separation" means the separation of components of a given sample by taking advantage of differential size, physical characteristic(s) or chemical characteristic(s) of the various molecules contained within that sample. The term "column" encompasses any container, usually but not necessarily cylindrical in shape, having total depth of at least one centimeter and preferably greater than two centimeters. The terms "homogeneous" or "substantially homogeneous" which are used in this specification to refer to the solid stationary phase means that the stationary phase is of a uniform substantially uniform structure and/or composition in a plane transverse to the flow of sample through a column.

Figure 1:
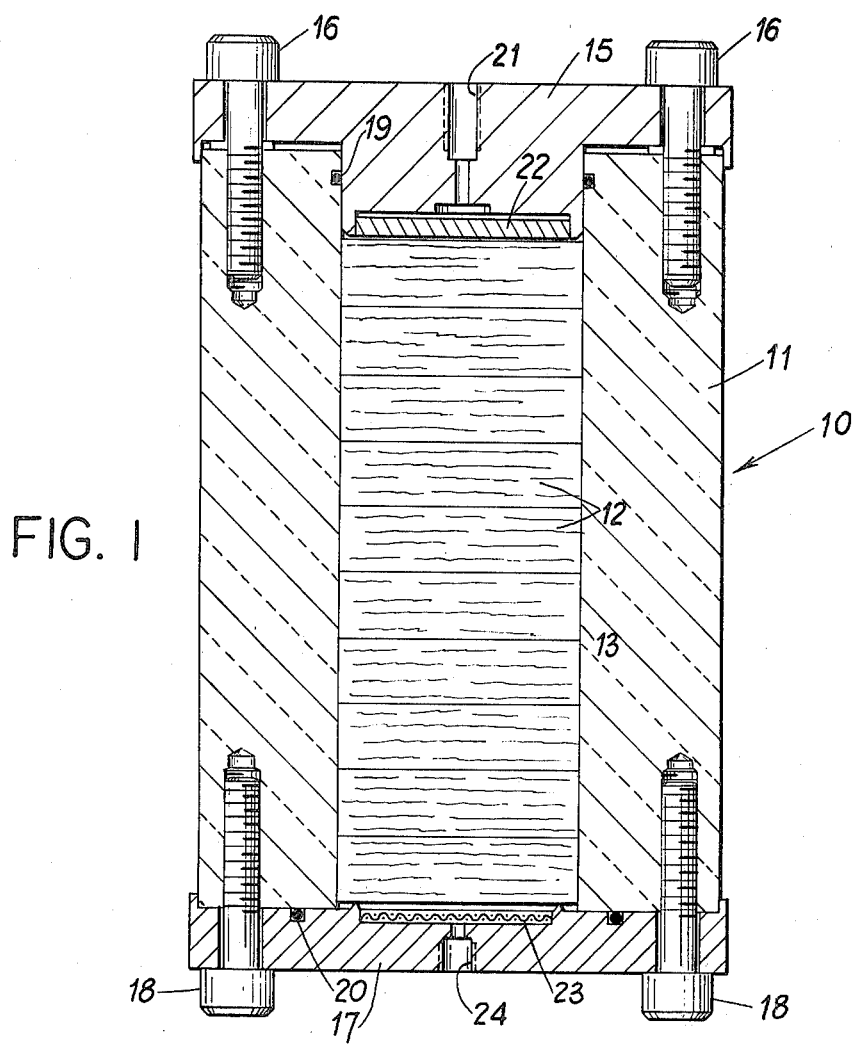
FIG. 1 is a sectional elevational view of an embodiment of a packed molecular separation column in accordance with the present invention.

FIG. 1 shows a preferred molecular separation column (10) for effecting differential distribution of a sample components between two phases in accordance with the present invention. The column (10) is a hollow cylinder (11) of circular cross-section which can be fabricated from any suitable material such as glass, steel, plexiglass and the like containing a number of discs of solid stationary phase elements (12). The edges (13) of the elements (12) form a fluid-tight seal with the interior wall of cylinder (11). The fluid-tight seal can be achieved in several ways. In one embodiment, the dimensions of the elements (12) and the interior of the cylinder (11) are such that the elements (12) are held firmly in place by a friction fit such that a pre-load compresses the elements. This requires very precise dimensional tolerances for both the interior wall of cylinder (11) and the elements (12). The individual elements (12) are inserted in the cylinder (11) usually with some mechanical aids such as a push-rod or piston. In a preferred embodiment which is suitable when an aqueous mobile phase is being passed through the column, the elements (12) are hydrophillic and swell somewhat upon contact with the mobile phase forming the required fluid-tight seal with the interior wall of cylinder (11). In such case, the dimensional tolerances of the interior surface of the cylinder and the elements (12) need not be as precise as in the case of a friction fit.

The column (10) includes an inlet cap (15) held in place by bolts (16) and an outlet cap (17) held in place with bolts (18). Inlet cap (15) is maintained in spaced relationship with cylinder (11) by spacer elements. Gasket rings (19) and (20) maintain an air-tight seal of caps (15) and (17) with cylinder (11). Inlet cap (15) is provided with an inlet orifice (21) for receiving liquid introduced into the column and inlet diffuser (22) for distributing the incoming liquid across the bore of the cylinder. Outlet cap (17) is provided with a support screen (23) to retain elements (12) within the column and an outlet orifice (24) through which the separated liquid is discharged to a sample detector for analysis.

Figure 2:
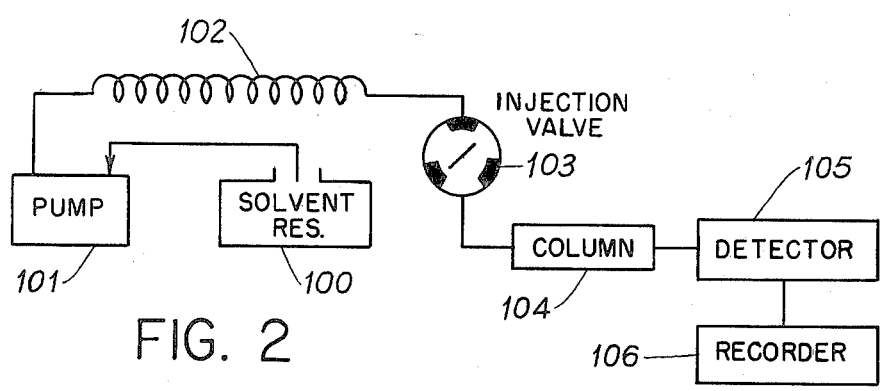
FIG. 2 is a block diagram illustrating the use of the molecular separation column of FIG. 1 in accordance with the present invention.

FIG. 2 is illustrative in diagrammatic form of the use of the column of FIG. 1. Suitable solvents, such as Fisher Scientific and MCB High-Pressure Liquid Chromatography (HPLC) grade solvent, can be circulated from a solvent reservoir (100) by a constant volume pump (101) which provides a flow of 1–12 ml/min. such as is available from AMF Cuno Division. A pulse dampener (102), which can be a two meter length of 0.16 cm o.d. $\times$ 0.08 cm i.d. stainless steel tubing followed by a tee union with a pressure gauge, interconnects the pump (101) with a Valco six port injection valve (103) at the head of a column (104). Suitable detectors (106) for the effluent include a Pharmacia 254 UV detector for efficiency studies and phenol separations and a Varian (Palo Alto, California) Vari-chrom UV Visible Spectral Photometer for capacity studies and separations requiring wavelengths other than 254 nm. A variable range strip chart recorder (106) can enable the use of either detection system.

Figure 3:
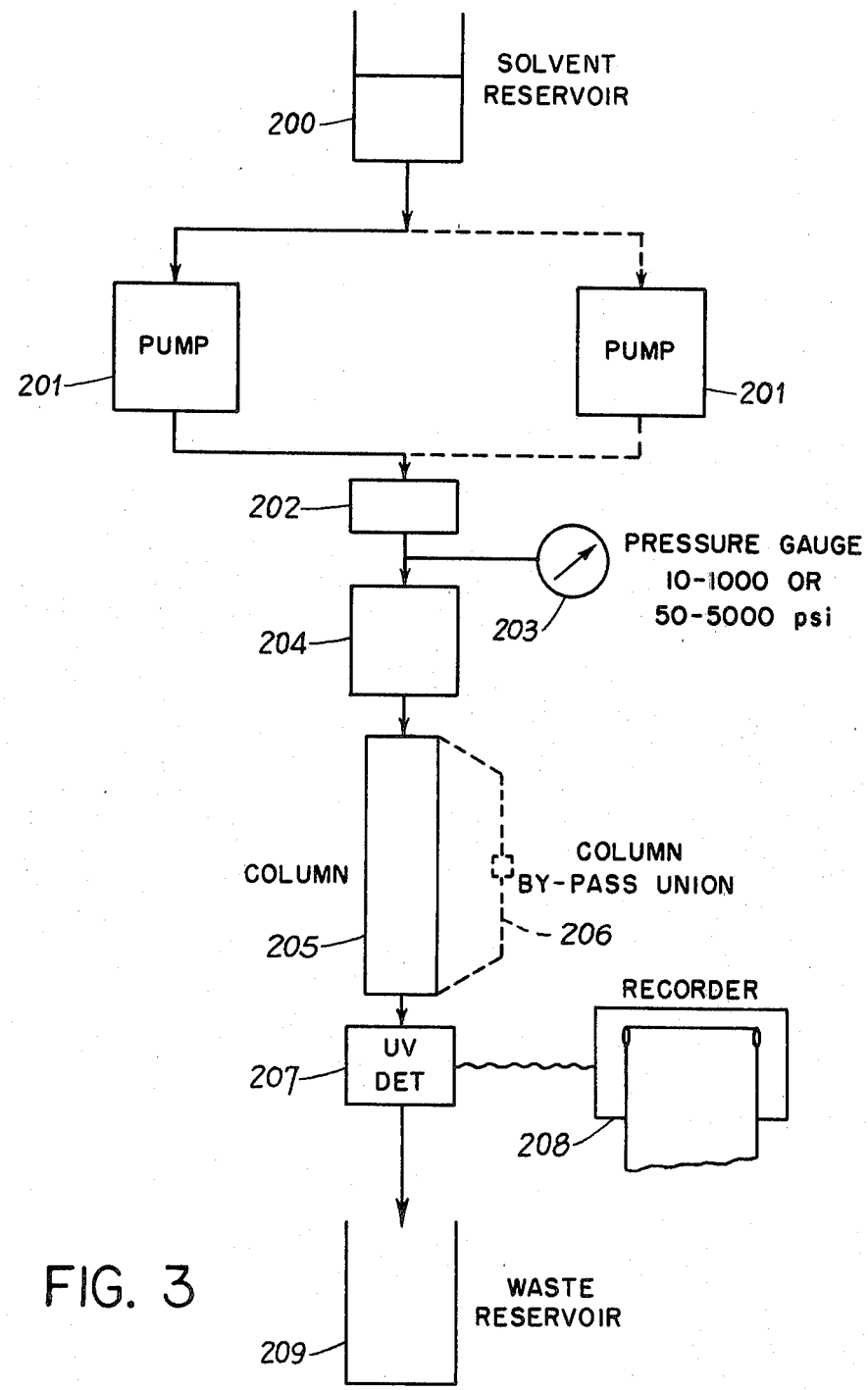
FIG. 3 is a block diagram of a second embodiment illustrating the use of a molecular separation column in accordance with the present invention.

FIG. 3 is illustrative in diagrammatic form of another embodiment of the use of a column in accordance with the present invention. A solvent from a suitable reservoir (200) is circulated by one or more high pressure pumps (201) which can be connected in series or in parallel to a high pressure pulse dampener (202), a Bourdon-type pressure gauge (203) and a valve-loop injector (204) into a column (205) which is fitted with a bypass circuit (206). The column effluent is passed to a 254 nm fixed wave length filter photometer (207), which is connected to a suitable recorder (208), and the effluent is then passed to a waste reservoir (209).

The stationary phase comprises a porous matrix of fiber having particulate immobilized therein, wherein at least one of said fiber or particulate is effective for molecular separation. The porous matrix is substantially homogeneous with respect to each component thereof. Preferably the particulate is effective for molecular separation. The molecular separation particulate should be contained in the stationary phase at an effective amount to achieve the desired molecular separation. Preferably the porous matrix is substantially inert and dimensionally stable. FIG. 1 illustrates the use of a plurality of disc-shaped elements but a single column element of equivalent length can also be used if so desired.

The preferred particulates which can be used in the present invention include all of those substances which can be provided in finely divided form and exhibit chromatographic functionality, i.e. capable of effective molecular separations. Mixtures of such compositions may also be utilized. Exemplary of such particulates are silica, alumina, diatomaceous earth, perlite, clays such as vermiculite, carbon such as activated carbon, modified polymer particulates such as ion exchange resins, crystalline cellulose, molecular sieves, and the like, the surfaces of which may be modified in conventional manner.

Such materials are commercially available under a variety of trademarks such as Biosila, Hi-Flosil, Li-Chroprep Si, Micropak Si, Nucleosil, Partisil, Porasil, Spherosil, Zorbax Sil, Corasil, Pallosil, Zipax, Bondapak, LiChrosorb, Hypersil, Zorbax, Perisorb, Fractosil, Corning Porous Glass, Dowex and Amberlite resins and the like.

Examples of references which describe particulates effective for molecular separations are the following:

U.S. Pat. No. 3,669,841 to Miller;
U.S. Pat. No. 3,722,181 to Kirkland et al;
U.S. Pat. No. 3,795,313 to Kirkland et al;
U.S. Pat. No. 3,983,299 to Regnier;
U.S. Pat. No. 4,029,583 to Chang;
U.S. Pat. No. 3,664,967 to Stehl;
U.S. Pat. No. 4,053,565 to Krekeler; and
U.S. Pat. No. 4,105,426 to Iher.

The entire disclosures of all of these references are incorporated herein by reference.

The particle size of the particulate is not critical but influences somewhat the flow rate at which the sample to be treated passes through the present columns. Usually, uniform particle sizes greater than about 5 microns are preferred with about 10–100 microns constituting a practical operational range. The amount of the particulate can vary widely from about 10 weight percent up to 80 weight percent or more of the solid stationary phase. The optimum particulate concentration will vary depending on the molecular separation desired although, at present, the greater concentrations of particulate appear to be more desirable.

The porous matrix of fiber may be any matrix capable of immobilizing the particulate contained therein, i.e. capable of preventing significant particulate loss from the stationary phase and having a porosity which enables the fluid to pass through the column. Preferably, the porous matrix is comprised of a self-bonding matrix of fibers. Suitable fibers which may be used in the present invention include polyacrylonitrile fibers, nylon fibers, rayon fibers and polyvinyl chloride fibers, cellulose fibers, such as wood pulp and cotton, and cellulose acetate. The preferred stationary phase of this invention has a porous matrix comprised of a self-bonding matrix of cellulose fibers.

In order to provide a matrix which is a coherent and a handleable structure for commerce and industry, it is desirable that at least one of the components which go into forming the porous matrix is a long, self-bonding structural fiber. Such fiber gives the stationary phase sufficient structural integrity in both the wet "as formed" condition and in the final dried condition. Such a structure permits handling of the phase, and in particular sheets during processing and at the time of its intended use. Such fibers are typically available in diameters in the range of 6 to 60 micrometers. Wood pulp, for example, has fiber diameters ranging from 15 to 25 micrometers, and fiber lengths of about 0.85 to about 6.5 mm.

The preferred long self-bonding structural fibers are preferably obtained from normally dimensioned cellulose pulp such as manila hemp, jute, caroa, sisal, bleached or unbleached kraft, kozu and the like, which typically has a Canadian Standard Freeness of +400 to +800 ml. These long self-bonding fibers will constitute greater than 50% of the porous matrix, by weight, preferably about 66–90% of the porous matrix and most preferably 75–83%.

When the amount of particulate immobilized in the porous matrix is low, i.e. less than about 50% by weight of the media, it is preferred that the porous matrix be formed of a self-bonding matrix of normal cellulose pulp having a Canadian Standard Freeness of +400 to +800 ml.

In the preferred embodiment of this invention it is desirable to have a high amount of particulate, i.e. greater than about 50% by weight of the stationary phase, immobilized in the porous matrix. It is thus highly desirable to use the invention described in copending application U.S. Ser. No. 123,467 to Hou et al to maintain such high content of particulate in the stationary phase. The entire disclosure of this application is incorporated herein by reference. Broadly, a minor portion of cellulose pulp refined to a Canadian standard freeness of between about +100 and −600 ml is incorporated with a major portion of the normally dimensioned cellulose pulp (+400 to +800 ml). In particular, from about 1% to about 10% of the refined pulp and about 10% to about 30% of the normal cellulose pulp, by weight of the stationary phase, is contained in the stationary phase, the remainder being the particulate. Generally, the weight ratio of unrefined to highly refined pulp will range from about 2:1 to about 10:1, preferably 3:1 to about 5:1. Such a mixture of pulps permits the retention of fine particulates up to about 80% or more by weight of the stationary phase.

The amount of particulate in the stationary phase may be as little as 10% by weight of the solid phase up to about 80% by weight. Preferably, levels of about 50 to 80% by weight are employed.

Preferably, the sheets which form the stationary phase, are formed by vacuum-felting an aqueous slurry of such normal cellulose fibers, highly refined wood pulp and particulate. This forms a sheet having the particulate immobilized in a porous matrix. The sheet shows a uniform high porosity, fine pore-size structure with excellent flow characteristics and is substantially homogeneous with respect to the fiber and particulate.

The sequence of adding the required components to water to form the aqueous slurry appears to be relatively unimportant provided that the slurry is subjected to controlled hydrodynamic shear forces during the mixing process. Preferably, the refined pulp is added to a slurry of the unrefined pulp and then the particulate incorporated therein. The slurry is normally prepared at an about 4% consistency and then diluted with additional water to the proper consistency required for vacuum-felting sheet formation. This latter consistency will vary depending upon the type of equipment used to form the sheet. Typically the slurry is cast onto a foraminous surface, vacuum felted, and dried in the conventional manner. The flat, dimensionally stable sheet can be of any desired thickness and is then cut to the appropriate dimensions for each type of column. Alternatively, the elements, usually in the form of discs to accommodate a chromatographic column, can be produced by dry mixing and pressing. A column of the stationary phase can also be formed in situ, for example by a slurry packing technique.

Chemical binders and additives may be used in forming the solid stationary phase of this invention. However, there should not be any chemical treatment detrimental to molecular separation.

A preferred molecular separation column in accordance with the invention comprises a plurality of elements, i.e. cut discs or pads, packed into the column housing which is usually in the shape of a cylinder with a very precise internal diameter. The discs are cut to the same diameter as the cylinder and stacked in the cylinder to an appropriate height. The disc and cylinder should preferably be in interference fit such that the disc can be readily pushed into the cylinder to any requisite depth but should not fall under gravitational force. After the column is packed dry, a high pressure pump can be used to pump solvent through the elements stacked in the column. Preferably, the elements swell to form a substantially bypass-free edge seal to the cylinder wall. The solvent front is very even with little or no skewing. Because the individual elements are dimensionally stable, the column is not sensitive to orientation or handling which is a common and major problem with other chromatographic media, particularly organic gel media.

In general, the flow rates attainable with the molecular separation columns of this invention are substantially higher than those obtainable with conventional gel or packed particle columns. The present columns also have excellent capacity since the diameter of the column is almost unrestricted compared to conventional gel or particle columns.

The molecular separation columns of this invention may be used for the well-known molecular separations usually performed with conventional columns.

Additionally the columns of the present invention may be found useful in areas where conventional columns are impractical, see for example the aforementioned copending and related applications U.S. Ser. No. 278,982, "Process for Preparing a Zero Standard Serum" to Hou and U.S. Serial No. 238,686 "Tissue Culture Medium" to Cone et al.

Typically chromatographic separations prior to the present invention have led to the development of very fine, spherical in many cases, homogeneous solid stationary phase materials. Conventional theoretical analysis of chromatographic separations led to the conclusions that for high resolutions, practical pressure drop levels and useable flow rates, analytical type columns needed extremely small, spherical and uniform particles with very specific surface properties. The use of comparatively non-homogeneous particles, i.e. fiber and particulate, of wide size distribution, distributed in a bimodal (two size) fiber matrix, as is the stationary phase of the present invention, is in direct contradiction of everything known about chromatographic separations.

The variables for the stationary phase of this invention that should be considered are, inter alia:
(1) type of fiber or fibers used;
(2) aspect ratio (L/D) of each type of fiber (initial and after refining);
(3) volume percent of each component in mixture;
(4) type of particulate or particulate mixture used;
(5) diameter of particulate (if spherical ) or other measure of particle geometry (aspect ratio, etc.);
(6) solids level (S/L used in disc formation);
(7) ratio (R) of particulate size (diameter) to fiber diameter;
(8) type of resin or binder used (if any);
(9) surface modification of particulate (or of fiber) used;
(10) type of solution used for slurry (water, alcohol, solvent) to form sheets;
(11) slurry additives (wetting agents, impurities, etc.); and
(12) felting conditions.

If one assumes that the stationary phase of this invention will be designed using a fiber matrix (e.g. refined pulp and highly refined pulp) and surface active particulate or particulate mixture chemically treated or derivatized prior to use for specific surface properties, including or not including the fiber, if desired, and binder systems, then the following simplified discussion will assist one skilled in the art in the design of the stationary phase.

A stationary phase with a high bulking factor is desirable. An open or porous matrix with high compression strength is needed for high flow rate at low pressure drops. These properties are primarily determined by the fiber matrix and must be consistent with holding the particulate in the structure. Therefore, the optimum mixture will vary from particulate to particulate.

Figure 4A:
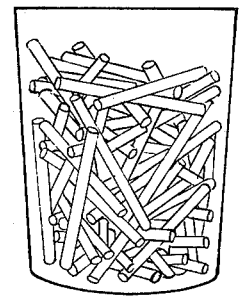
FIGS. 4A and 4B show simple fiber/fiber packings.
Figure 4B:
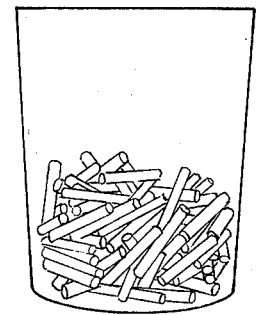

If one assumes for discussion sake that the fibers are rigid rods of various L/D ratios and that the particulate additives are spherical in nature, the problem of stationary phase design from a structural standpoint becomes one of understanding the packing of fibers with fibers and fibers with spheres. Simple fiber/fiber packings are shown in FIGS. 4A and 4B. The density of a simple fiber system is a function of the fiber L/D ratio, with low L/D ratios leading to higher densities or lower interstitial volumes. The bulk volumes as a function of L/D ratio for various rigid fibers is known. The bulk volume is essentially independent of the fiber material (low modulus flexible fibers will have a different effect). If fiber mixtures are considered, the problem is somewhat more complicated and the resulting packing efficiency is determined by the ratio of the fiber L/D ratios. For fibers of the same diameter, fibers short enough to fit into the interstitial volume of the longer fibers will create a lower bulk density material. Certain other fiber size ratios can increase or decrease the resulting bulk volume.

Uniform spheres, if allowed to pack gravitationally, will form hexagonal packed layers. Table 1 shows the effect of sphere diameter on the occupied volume, the interstitial volume, the surface area, and surface to interstitial volume ratio.

TABLE 1

| HEXAGONAL PACKED SPHERES COLUMN 7.6 cm DIA., 30.5 cm LONG | | |
|---|---|---|
| | 0.3 cm SPHERES | 0.15 cm SPHERES |
| OCCUPIED VOLUME, cm$^3$ | 871.5 | 836.5 |
| INTERSTITIAL VOLUME V$_1$ cm$^3$ | 517.9 | 552.3 |
| SURFACE AREA (S), cm$^2$ | 16588 | 31850 |
| S/V$_1$ | 78.5 | 145 |

As expected, the surface to interstitial volume increases dramatically for smaller diameters. While the total interstitial volume increases only slightly. What is not shown in this table, however, is that while the interstitial volume increases only slightly, the path through the interstitial volume becomes much more tortuous because each component in the path becomes much smaller (leading to higher pressure drops for smaller diameter particles). The ratio of interstitial volume to surface area is important since this is the factor which primarily determines the equilibrium distribution of material from the liquid phase to the solid surfaces in a typical chromatographic column. This simple sphere packing picture indicates why uniform spheres of small diameter give more useful columns as long as the pressure drop does not become excessive. Typically, particle diameters from 5–10 um are common in liquid chromatography. If small spheres are mixed with large spheres the bulk volume is a function of their diameter and volume fractions.

If simple uniform fibers are packed with uniform spheres, the efficient sphere packing is abruptly interrupted and the bulking factor is a function of fiber L/D ratio and the ratio R of sphere diameter to fiber diameter and the volume fraction of each component. This is shown in Table 2 which indicates the large density differences that are possible with composite blends depending upon the size and amount of each component.

TABLE 2*

THEORETICAL % SOLID CONTENT FOR FIBER-SPHERE PACKING

| % Fiber Loading | R | L/D 1.00 | 2.00 | 3.91 | 7.31 | 15.51 | 24.49 | 37.10 |
|---|---|---|---|---|---|---|---|---|
| 10 | R = ∞ | 68.5 | 68.5 | 68.5 | 68.5 | 68.5 | 68.5 | 61.0 |
|  | R = 0 | 64.1 | 64.1 | 64.1 | 64.1 | 64.1 | 64.1 | 64.1 |
| 20 | R = ∞ | 77.0 | 77.0 | 77.0 | 77.0 | 69.0 | 56.2 | 44.3 |
|  | R = 0 | 66.7 | 66.7 | 66.7 | 66.7 | 66.7 | 66.7 | 66.7 |
| 30 | R = ∞ | 87.7 | 87.0 | 83.3 | 77.5 | 60.0 | 46.2 | 34.5 |
|  | R = 0 | 69.5 | 69.5 | 69.5 | 69.5 | 69.5 | 68.5 | 45.5 |
| 40 | R = ∞ | 85.5 | 83.3 | 78.7 | 72.0 | 52.9 | 39.1 | 28.6 |
|  | R = 0 | 72.5 | 72.5 | 72.5 | 72.5 | 72.5 | 51.3 | 34.2 |
| 50 | R = ∞ | 82.7 | 80.6 | 74.6 | 67.2 | 47.2 | 34.1 | 24.2 |
|  | R = 0 | 76.4 | 76.4 | 76.4 | 76.4 | 62.5 | 41.2 | 27.5 |
| 60 | R = ∞ | 80.0 | 77.5 | 71.0 | 62.9 | 42.7 | 30.2 | 21.0 |
|  | R = 0 | 80.0 | 80.0 | 80.0 | 80.0 | 51.8 | 34.2 | 23.0 |
| 70 | R = ∞ | 77.5 | 74.6 | 67.6 | 59.2 | 39.1 | 27.0 | 23.0 |
|  | R = 0 | 84.0 | 84.0 | 84.0 | 72.5 | 44.5 | 29.4 | 19.7 |
| 80 | R = ∞ | 74.6 | 72.0 | 65.0 | 56.2 | 36.0 | 24.5 | 16.7 |
|  | R = 0 | 88.5 | 84.0 | 74.6 | 63.3 | 39.0 | 25.8 | 17.5 |
| 90 | R = ∞ | 72.5 | 69.5 | 62.2 | 53.2 | 33.4 | 22.4 | 15.1 |
|  | R = 0 | 78.7 | 74.6 | 66.2 | 56.2 | 34.5 | 23.0 | 15.4 |
| 100% Fiber |  | 70.5 | 67.1 | 59.5 | 50.3 | 31.1 | 20.7 | 13.8 |
| 100% Spheres |  | 61.5 | 61.5 | 61.5 | 61.5 | 61.5 | 61.5 | 61.5 |
| Theoret. Max. |  | 88.5 | 87.4 | 84.4 | 80.6 | 73.5 | 69.5 | 66.7 |

*Milewski, John V., "Identification of Maximum Packing Conditions in the Bimodal Packing of Fibers and Spheres," 29th annual Reinforced Plastics Composites Conference, February 1974

If the mixture consists of fiber size mixtures (various L/D) and sphere size mixtures (bimodal, trimodal, etc.), the packing density becomes a complicated functional relationship to find more optimum materials. Higher bulk volume leads to high flow rate but there is a trade off with compression strength. Other particle shapes and other fiber modulus (i.e. non-rigid fibers) will add their own complexity.

If one starts with a column of packed uniform spheres and adds a small amount of fiber, it takes very little fiber to create a large change in the interstitial volume of the resulting mix. The ratio of interstitial volume to surface area will increase as will the size of the individual volumes contributing to the total interstitial volume. This will lead to higher flow rates but at the expense of the distribution equilibrium responsible for the component separation. The literature is not clear as to the relative magnitude of these effects. There may be a regime of high interstitial volume consistent with good uniform distribution of the active particulate but at a ratio of interstitial volume element to particle surface area that is still consistent with good media separation properties. These structure changes will influence the distance over which diffusion takes place, the degree of mixing and flow turbulence, the tortuosity of the liquid path and other properties. Therefore, optimum structures for each specific system is to an extent empirical.

Notwithstanding theoretical explanations of the manner of operation, the present columns are characterized by a substantially reduced pressure drop and more uniform chromatographic peaks. The present columns are eminently suited for preparative chromatography as well as for analytical chromatography.

In order to further illustrate the invention, various examples are given below. It will be appreciated that in these examples, as throughout this specification and claims, all parts and percentages are by weight and all temperatures in degrees Celsius unless otherwise indicated.

EXAMPLE 1

Weyerhauser Coho bleached Kraft, mean diameter about 20 microns, mean length about 0.16 cm, Canadian Standard Freeness +600 ml. was refined in a Black Claussen twin disc refiner to a Canadian Standard Freeness of −250 ml. The refined pulp, unrefined pulp and an unmodified silica gel about 15 microns in diameter were added to water with strong agitation to form an aqueous slurry of about 4% consistency. The slurry was diluted to 2% consistency and then vacuum felted in an about 16 cm diameter hand sheet apparatus using a 100 mesh screen. The sheet was removed from the apparatus and dried in a static oven at about 175° C. until a constant weight was achieved. The sheet contained 70% of the silica particulates and 30% wood pulp fiber (24% unrefined pulp and 6% highly refined cellulose pulp). The particulate was Syloid (W. R. Grace) 620 having a nominal average particle size of 15 microns, a surface area of 320 $M^2/g$ and a pore volume of 1.1 ml/g.

Discs were prepared and packed into a 50 cm precision bore stainless steel tube having a 10 mm inner diameter using a 9.5 mm diameter wood dowel. The discs were individually packed by hand into the column with the screen side down and efforts were made to compress each disc to the same degree.

Examination of the silica by scanning electron microscopy revealed the presence of silica particles ranging in size from 1–40 microns, a feature which is generally unsuitable for chromatographic use due to high pressure drop and non-peak symmetry produced by a packed bed of heterogeneously sized particles. The entire particle size range remained entrained in the cellulose matrix. Some silica was lost during the felting process such that the final composite contained 64% particulate. It was observed that the silica particles appear to be bound together by the small, highly refined pulp and such fibers may, in fact, be chemically bound to the silica surface at the points of contact. The completely packed column contained 15.7 grams of the composite material and a void volume of 32.5 ml, i.e. 83% of the total column volume.

Figure 5:
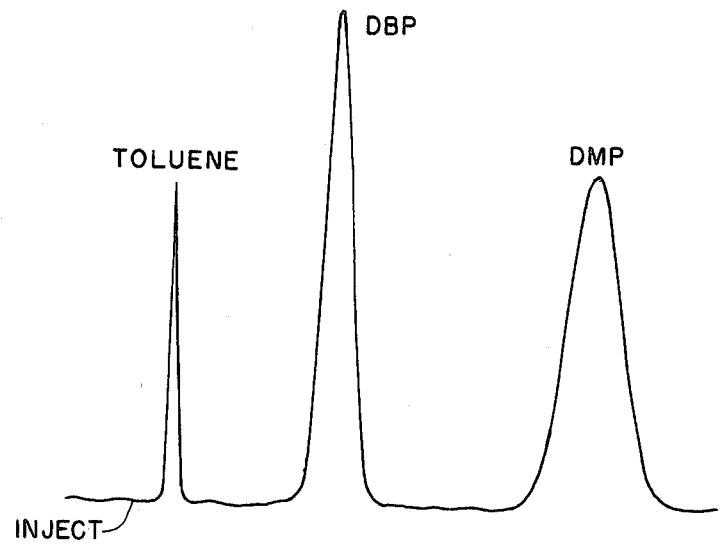

A test mixture containing three components was prepared. The components were chosen to provide information on peak dispersion for non-retained ($k'=0$, toluene), slightly retained ($k'=2$-3, dibutylphthalate "DBP") and well-retained ($k'=5$-6, dimethylphthalate "DMP") solutes. The mobile phase composition (0.2% isopropanol in heptane) was adjusted to give the appropriate retention for these components on the stationary phase. The column was tested at flow rates of 0.2-19.9 ml/min. and the chromatographic characteristics (pressure drop, capacity factor and H) were calculated and the results are set forth in Table 3 below. The high degree of peak symmetry displayed by the composite column throughout the evaluation is illustrated by a representative chromatogram set forth in FIG. 5.

TABLE 3

| Flow Rate (ml/min) | Pressure Drop (kg/cm²) | Toluene t_m (min) | H (mm) | DBP k' | H (mm) | DMP k' | H (mm) |
|---|---|---|---|---|---|---|---|
| 0.2 | 2.1 | 166.43 | 0.51 | 2.3 | 0.65 | 5.6 | 0.85 |
| 0.5 | 4.2 | 65.46 | 0.57 | 2.1 | 0.79 | 5.2 | 0.85 |
| 1.0 | 8.05 | 32.48 | 0.65 | 2.2 | 0.90 | 5.5 | 0.87 |
| 2.0 | 15.75 | 16.83 | 0.71 | 2.1 | 0.97 | 5.4 | 0.98 |
| 4.0 | 29.75 | 8.46 | 0.73 | 2.1 | 1.05 | 5.4 | 1.06 |
| 6.0 | 44.8 | 5.69 | 0.79 | 2.1 | 1.12 | 5.5 | 1.09 |
| 8.0 | 59.5 | 4.31 | 0.75 | 2.2 | 1.17 | 5.7 | 1.09 |
| 9.0 | 72.8 | 3.48 | 0.79 | 2.5 | 1.40 | 6.0 | 1.06 |

The increase in pressure drop across the column was found to be a linear function of the flow rate (linear velocity) at pressures up to 70 kg/cm². While this is not surprising for particulate packed beds, it indicates that virtually no compression of the matrix occurred at these pressures. The column was also subjected to a pressure drop of 154 kg/cm² which corresponded to the maximum flow rate capability of the system (19.8 ml/minute). Subsequent reevaluation of the chromatographic parameters at a flow rate of 6 ml/minute gave values ($H_{DBP}=1.53$, $H_{DMP}=1.17$) only slightly poorer than those previously obtained (Table 3). A void of 2.5 mm was, however, noted at the inlet end of the column when the fitting was removed.

Figure 7:
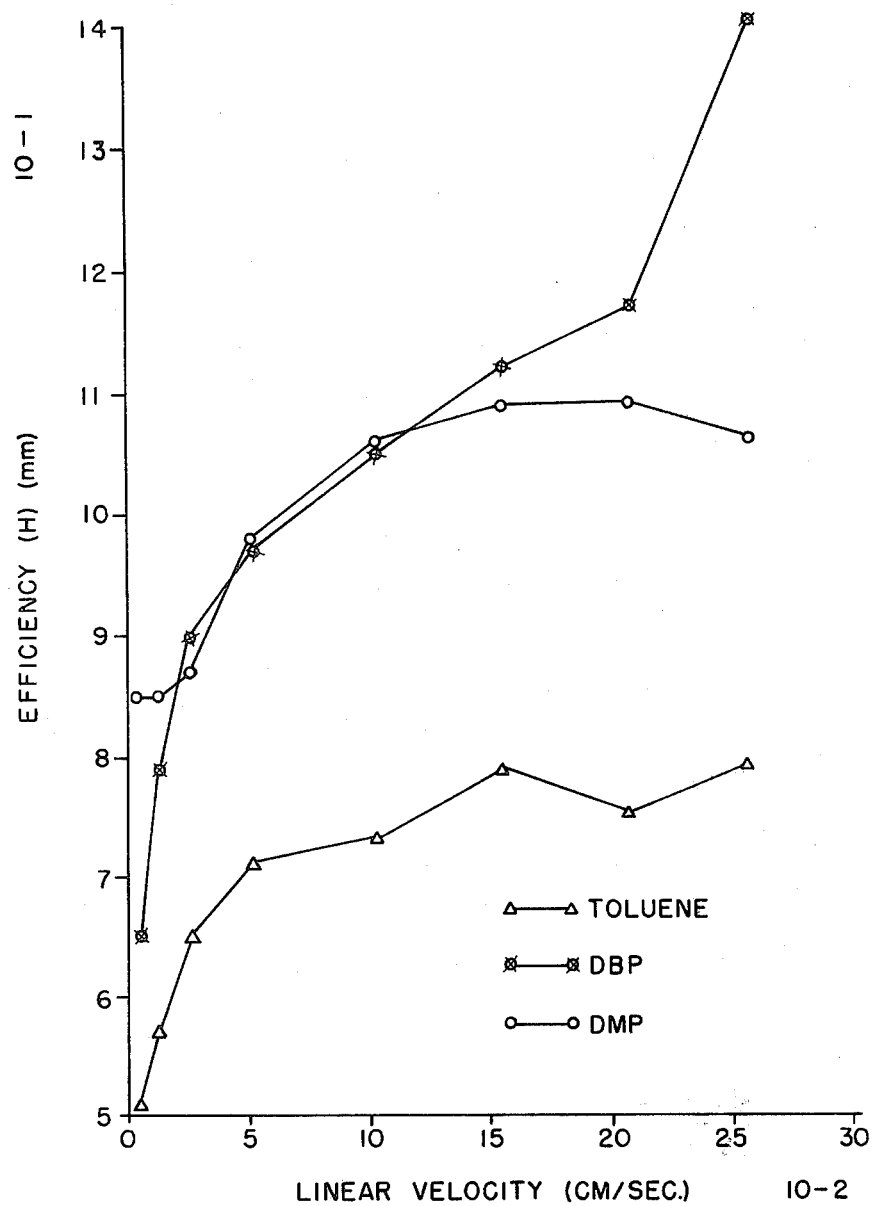
FIG. 7 is a plot of column efficiency as a function of linear velocity obtained from Example 1.
Figure 8:
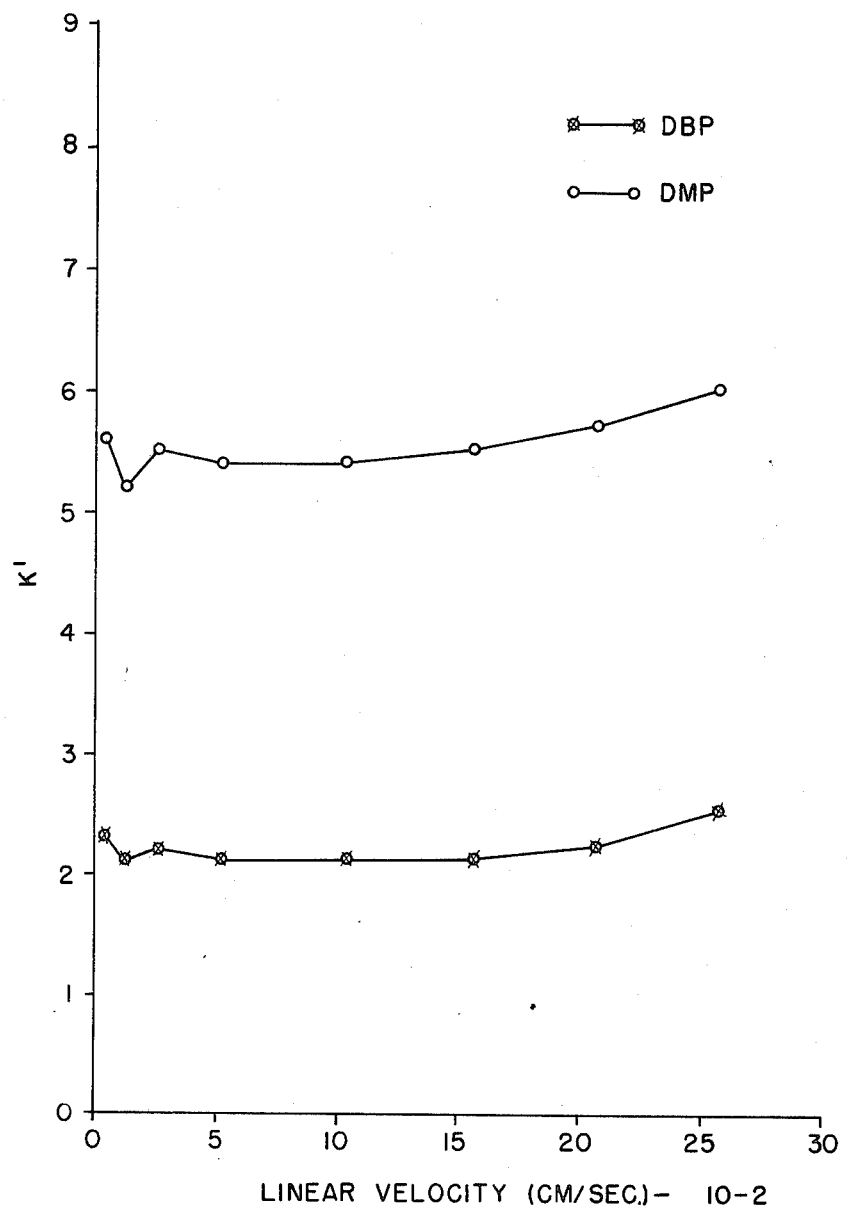
FIG. 8 is a plot showing the dependance of the factor (k') on linear velocity obtained from Example 1.

The influence of flow rate on chromatographic efficiency for the stationary phase is shown in FIG. 7. The general shape of the curves is similar to that obtained with packed columns of porous silica. Although the initial H increase for conventional columns is greater than for the porous matrix of this invention, this is offset somewhat by a later flattening of the curve at high flow rates. The efficiency of the column of the present invention in the region of relatively constant H corresponds roughly to that obtained with 30-35 micron porous silica particles and essentially no variation of the capacity factor was seen at the flow rates examined as indicated in FIG. 8.

EXAMPLE 2

Figure 6:
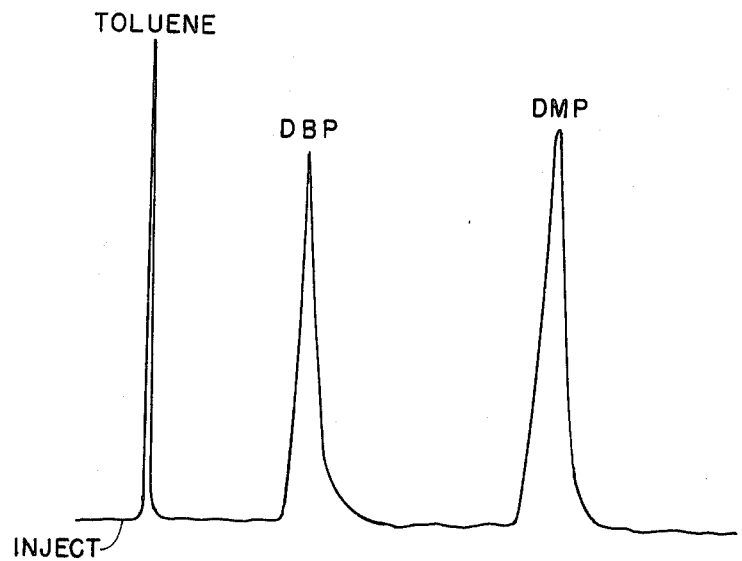
FIGS. 5 and 6 are chromatograms obtained in the separations of Examples 1 and 2.

For comparison, a 25 cm × 10 mm i.d. column was packed to contain 10.3 grams of the same silica particulate by a modified balance density slurry technique. This was approximately equivalent to the 10 grams of silica calculated to be contained in the 50 cm column described in Example 1. Peak symmetry obtained with this column was generally poor and indicated a rather heterogeneous packed bed. The packed particles apparently shifted somewhat during later use and pressures approaching the initial packing pressure (ca 350 kg/cm²) and the peak symmetry improved to that shown in FIG. 6. The chromatographic parameters calculated for the silica column are shown in Table 4 below.

TABLE 4

| Flow Rate (ml/min) | Pressure Drop (kg/cm²) | Toluene t_m (min) | H (mm) | DBP k' | H (mm) | DMP k' | H (mm) |
|---|---|---|---|---|---|---|---|
| 1.0 | 32.55 | 16.85 | 0.10 | 5.4 | 1.37 | 14.2 | 0.17 |
| 2.0 | 55.3 | 8.44 | 0.09 | — | — | — | — |
| 6.0 | 161.35 | 2.93 | 0.11 | 9.1 | 0.49 | 20.0 | 0.33 |
| 9.9 | 267.4 | 1.83 | 0.12 | 3.8 | 0.56 | 9.6 | 0.34 |
| 12.0 | 329 | 1.54 | 0.14 | 4.1 | 1.08 | 10.6 | 0.42 |

For further comparison, a composite containing 94% unrefined cellulose and 6% of the −250 ml Canadian Standard Freeness cellulose and no silica was evaluated in the 50 cm column. The calculated parameters are given in Table 5 below.

TABLE 5

| Flow Rate (ml/min) | Pressure Drop (kg/cm²) | Toluene t_m (min) | H (mm) |
|---|---|---|---|
| 0.2 | 2.1 | 125.86 | 3.68 |
| 0.5 | 4.9 | 49.39 | 4.10 |
| 1.0 | 8.4 | 24.61 | 4.20 |
| 2.0 | 16.1 | 12.60 | 4.63 |
| 4.0 | 30.1 | 6.46 | 4.59 |

The pressure drop was nearly identical to that of the composite containing particulate at all flow rates examined but the peak dispersion (H) for the unretained solute (toluene) was much greater. The phthalates were unretained on the porous cellulose matrix.

EXAMPLE 3

Chromatographic characteristics of additional solid stationary phase materials of the present invention were determined and the results are set forth in the following Tables 6-9:

TABLE 6

STATIONARY PHASE CONTAINS NOMINALLY 50% SILOID 620, 7.5% - 250 ml CSF PULP AND REMAINDER UNREFINED PULP

| Flow Rate (ml/min) | Pressure Drop (kg/cm²) | Toluene t_m (min) | H (mm) | DBP k' | H (mm) | DMP k' | H (mm) |
|---|---|---|---|---|---|---|---|
| 1.0 | 2.45 | 16.70 | 5.09 | 1.0 | 6.36 | 2.8 | 5.28 |
| 2.0 | 3.5 | 8.27 | 5.76 | 1.5 | 7.15 | 3.9 | 5.92 |
| 4.0 | 4.9 | 4.33 | 5.82 | 1.5 | 7.02 | 3.7 | 6.41 |
| 6.0 | 7.35 | 2.95 | 5.53 | 1.2 | 6.23 | 2.8 | 6.58 |
| 8.0 | 9.45 | 2.17 | 6.09 | 1.0 | 7.62 | 2.8 | 6.51 |
| 9.9 | 11.55 | 1.73 | 6.42 | 1.0 | 7.46 | 2.8 | 6.67 |

25 cm × 10 mm ID column containing 6.8 g of stationary phase material.
Void volume = 16.7 ml = 85% of total column volume.

TABLE 7

STATIONARY PHASE CONTAINED NOMINALLY 44% SILOID 620, 6% - 250 ml CSF PULP AND REMAINDER UNREFINED PULP

| Flow Rate (ml/min) | Pressure Drop (kg/cm²) | Toluene (mm) | H k' | DBP (mm) | H k' | DMP (mm) | H k' |
|---|---|---|---|---|---|---|---|
| 1.0 | 4.55 | 15.60 | 2.33 | 1.0 | 2.91 | 2.6 | 2.51 |
| 2.0 | 7.35 | 7.87 | 2.49 | 1.1 | 3.27 | 3.0 | 2.72 |
| 4.0 | 12.25 | 4.04 | 2.68 | 1.1 | 3.36 | 3.0 | 2.73 |
| 6.0 | 18.2 | 2.76 | 2.66 | 1.1 | 3.45 | 3.0 | 2.87 |
| 8.0 | 23.8 | 2.05 | 2.65 | 1.1 | 3.52 | 3.0 | 2.94 |
| 9.9 | 29.4 | 1.65 | 2.66 | 1.1 | 3.01 | 3.0 | 2.97 |

25 cm × 10 mm ID column containing 8.9 g of stationary phase material.
Void volume = 15.6 ml = 80% of total column volume.

TABLE 8

STATIONARY PHASE CONTAINED NOMINALLY 19% SILOID 620, 6% CSF PULP AND REMAINDER UNREFINED PULP

| Flow Rate (ml/min) | Pressure Drop (kg/cm²) | Toluene t_m (min) | H (mm) | DBP k' | H (mm) | DMP k' | H (mm) |
|---|---|---|---|---|---|---|---|
| 1.0 | 3.85 | 14.76 | 0.54 | 0.7 | 1.16 | 1.9 | 0.81 |
| 2.0 | 6.65 | 7.48 | 0.55 | 0.7 | 1.31 | 1.9 | 0.85 |
| 4.0 | 10.85 | 3.78 | 0.59 | 0.7 | 1.49 | 1.9 | 0.91 |
| 6.0 | 16.1 | 2.56 | 0.62 | 0.7 | 1.49 | 1.9 | 0.97 |
| 8.0 | 21 | 1.89 | 0.64 | 0.7 | 1.59 | 2.0 | 0.99 |

TABLE 8-continued

STATIONARY PHASE CONTAINED NOMINALLY
19% SILOID 620, 6% - 250 CSF PULP
AND REMAINDER UNREFINED PULP

| Flow Rate (ml/min) | Pressure Drop (kg/cm$^2$) | Toluene $t_m$ (min) | H (mm) | k' | DBP H (mm) | k' | DMP H (mm) |
|---|---|---|---|---|---|---|---|
| 9.9 | 25.9 | 1.56 | 0.61 | 0.7 | 1.67 | 1.9 | 1.04 |

25 cm × 10 mm ID column containing 9.9 g of stationary phase material.
Void column = 14.8 ml = 76% of total column volume.

TABLE 9

STATIONARY PHASE COMPOSITE CONTAINED
NOMINALLY 30% SILOID 620, 10% - 250 CSF PULP,
AND REMAINDER UNREFINED PULP

| Flow Rate (ml/min) | Pressure kg/cm$^2$ | Toluene $t_m$ (min) | H (mm) | k' | DBP H (mm) | k' | DMP H (mm) |
|---|---|---|---|---|---|---|---|
| 1.0 | 4.55 | 15.60 | 2.33 | 1.0 | 2.91 | 2.6 | 2.51 |
| 2.0 | 7.35 | 7.87 | 2.49 | 1.1 | 3.27 | 3.0 | 2.72 |
| 4.0 | 12.25 | 4.04 | 2.68 | 1.1 | 3.36 | 3.0 | 2.73 |
| 6.0 | 18.20 | 2.76 | 2.66 | 1.1 | 3.45 | 3.0 | 2.87 |
| 8.0 | 23.8 | 2.05 | 2.65 | 1.1 | 3.52 | 3.0 | 2.94 |
| 9.9 | 29.4 | 1.65 | 2.66 | 1.1 | 3.01 | 3.0 | 2.97 |

25 cm × 10 mm ID column containing 8.9 g of stationary phase.
Void volume = 15.6 ml = 80% of total column volume.

EXAMPLE 4

Using the column of Example 1, and the arrangement shown in FIG. 3, separations of phenols and phthalates were effected. The efficiency and capacity data obtained are set forth in FIGS. 9 and 10, respectively.

Figure 9:
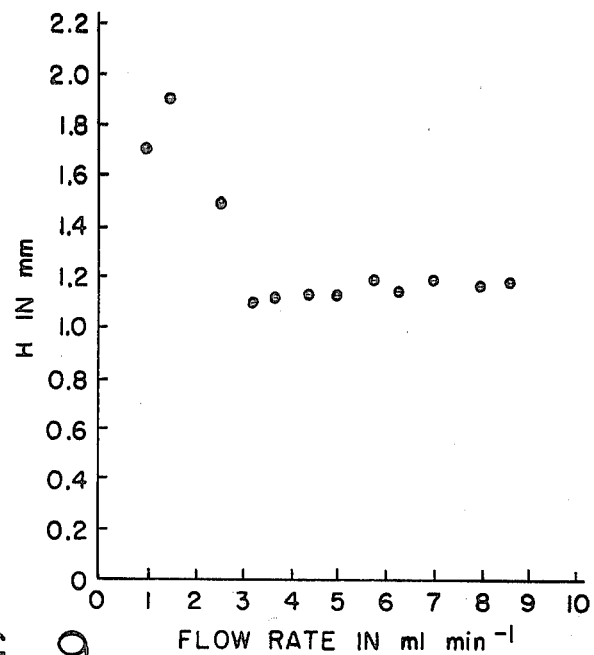
FIGS. 9 and 10 set forth van Deemter plots (sorptive efficiency) and capacity data for a stationary phase of the present invention obtained from Example 4.

The phenols were separated using 1% isopropyl alcohol in chloroform as a mobile phase which yielded a solvent strength greater than the required 0.3 to elute phenols from silica. The flow rate was 3.2 ml/min. and the components varied between 10 and 25 mg. The components eluted in the order of benzene, o-chlorophenol, p-phenylphenol, phenol and p-nitrophenol. Resolution of the first two components was approximately 90%, the third and fourth components approximately 80% and the final compound greater than 98%. Although the phenol and p-phenylphenol appeared as a single peak in the mixture chromatogram, the chromatogram for the pure components indicated a retention difference of 30 mm at a chart speed of 48.6 cm/hour. When the pure component chromatograms were overlaid, a resolution of 88% was observed. The most striking aspect of the van Deemter plot shown in FIG. 9 is the shape of the curve. Normally for liquid chromatography, H values are expected to decrease at low flow rates. It has also been reported in the literature that at very low flow rates, the H values can begin to decrease and then increase sharply. As can be seen in FIG. 9, as the flow rate decreases, the H values decrease, increase sharply and finally decrease again, a type of behavior that has not previously been reported.

Figure 10:
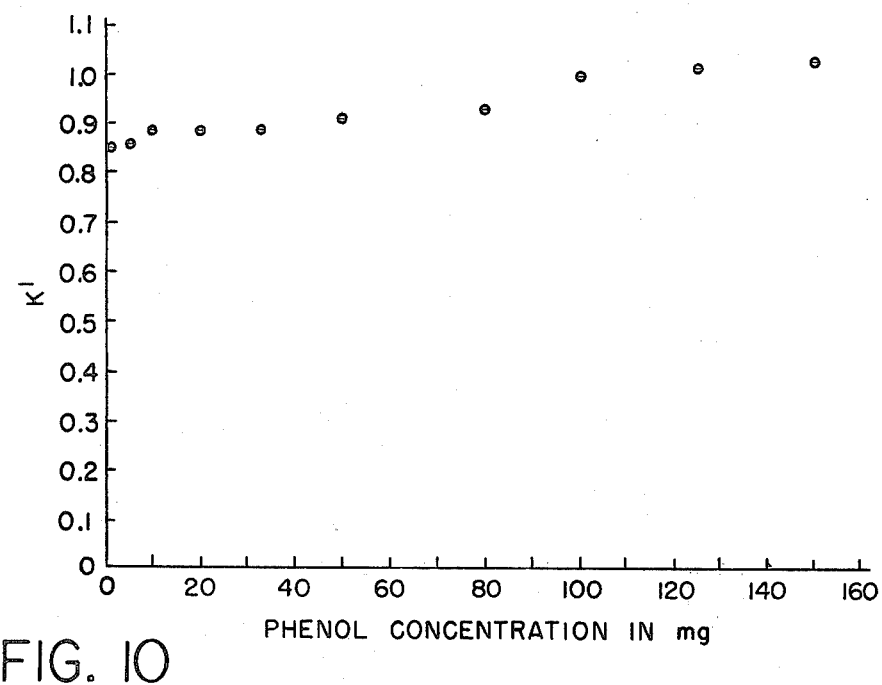

The second set of chromatograms were obtained with the separation of dimethyl, diethyl, dibutyl and dioctyl phthalates. The solvent system used was 7% chloroform in hexane, the flow rate was 3.8 ml/min. and the chart speed was 40.6 cm/hr. The compounds eluted in the order of decreasing molecular weight. The resolution for octyl and butyl phthalate was 95% or better; the resolution of the latter two compounds was 92-94%. The peaks in the mixture chromatogram represented 18-22 mg of each compound. FIG. 10 shows that the stationary phase of the present invention had at least a 100 mg capacity.

EXAMPLE 5

Following the procedures and using the columns described in Example 4, the column parameters for a 99% separation of the phthalates with a 3.15 cm/min. flow rate were determined. With the stationary phase containing nominally 70% particulate, the separation time was 2.38 minutes, the pressure drop was about 9.4 kg/cm$^2$, the distance the mobile phase traveled was 5.71 cm and the total quantity of particulate was 1.14 grams. For the silica particulate column, the separation time was 1.08 minutes, the pressure drop was about 20.6 kg/cm$^2$, the distance the mobile phase traveled was 1.54 cm and the total amount of particulate was 0.705 gram. Substantially longer columns are required with the stationary phase of the present invention for the same degree of separation produced by a 100% particulate column. The additional column length, however, is more than offset by low pressure drops for the separation. In commercial separations, the pressure drop characteristics of the separation media is extremely important since excessively high pressure drops can limit the throughput of the column requiring expensive pumps and materials or place a restraint on column length and thus the number of theoretical plates available for a given separation. Since the stationary phase of the present invention has a substantially lower pressure drop than the 100% particulate column, much longer column lengths are possible.

EXAMPLE 6

This example illustrates the effect that the composition of the materials used in producing the solid stationary phase has upon the chromatographic effectiveness of the resulting stationary phase.

Eight aqueous mixtures of silica gel, long cellulosic fibers, and highly refined pulp were prepared, and the mixture was agitated for uniformity. The aqueous suspensions were then poured into a filter mold, removing the water and forming a composite material felt. Eight felts were produced according to the experimental design presented in Table 10, with specific composition of the materials charged into the aqueous suspension presented in Table 11. The eight felts were then removed from the filter and dried. Plugs (10 mm in diameter) were cut from the dried composite felt and packed into 250 mm stainless steel columns with conventional preparative high performance liquid chromatographic end fittings. The chromatographic evaluations of the thus formed stationary phases were carried out using a mobile phase of 0.2 percent 2-propanol/heptane. The pressure drop and the dispersion characteristics of the 10 mm i.d. columns were evaluated at flow rates of 0.2, 6, and 19.8 ml per minute. The dispersion characteristics for the stationary phases were determined using an unretained solute (toluene), a slightly retained solute (dibutyl phthalate, "DBP") and a well retained solute (dimethyl phthalate, "DMP"). The experimental results of the preparation of the fiber particulate materials as well as the chromatographic effectiveness of these materials are presented in Tables 12 through 15. The effects of each of the composition variables on each set of the experimental results were then obtained with a conventional statistical analysis of the screening design. The effect of a variable was the difference between the average experimental result when the independent variable was positive and the average value of the experimental results when the independent variable was negative. The variable levels chosen for run 8 were arbitrarily defined as the negative levels of those variables in this design. The significance of the effects was estimated by comparing the effects of the independent variables to the effects obtained with the dummy variable. The effect of the dummy variable is due to experimental error as well as variable interactions. Because of the strong interactions that are potentially present in this screening design, the effects of particle size, the dispersity of the particle size distribution, and the presence of mixtures in the particulate were also included in the estimate of the effects due to experimental error and variable interactions. This results in a conservative estimate of the probability for significance, and the significance of the effects could be substantially greater than appears in the tables. The analyses of the effects of the variables are presented in Tables 17 through 38.

Each of the variables that were investigated were significant in influencing the chromatographic performance of the stationary phase. Some of the compositional variables improved some of the experimental results but resulted in decreased performance in other areas. A summary of the effects of the composition of the stationary phase on some of the more important experimental results is provided in Table 38.

As ther particle size of the Partisil brand porous silica was decreased from 10 microns to 5 microns, there was a greater weight loss of the composite material during formation, the drainage time was reduced, the pressure drop through the sheet was greater, and the height equivalent of a theoretical plate (H in mm) was lower. The product of the pressure drop and height equivalent of the theoretical plate was increased. The overall resolution of the column was not significantly increased by the change in particle size of the Partisil. When the runs based on Partisil were compared with the runs based on Siloid 620 brand silica, the Partisil decreased the felt drainage time and the resolution of the column. The height equivalent of theoretical plate as well as the product of the pressure drop and height equivalent of the theoretical plate was greater for the columns based upon Partisil than the columns based upon Syloid 620. When Partisil was present as a mixture with Syloid 620, the mixture had both lower pressure drops and lower height equivalent of theoretical plates in the composite material than when either pure Syloid 620 or pure Partisil was used as the particulate. The resolution of the columns when mixtures of Partisil and Syloid 620 were present was improved while the product of the pressure drop and height equivalent of the theoretical plate was reduced, the weight loss associated with the composite material formation increased, the felt drainage decreased, and the height equivalent of the theoretical plate decreased. There was little effect on the pressure drop, the resolution, and the product of the pressure drop and the height equivalent of the theoretical plate. There was a modest effect of the amount of the refined pulp on the capacity factor for the dimethyl phthalate. The freeness of the pulp was a significant variable since the runs with the higher freeness values i.e. more positive CSF had lower weight loss, lower drainage time in the felt formation, lower pressure drop, and poor resolution with increased height equivalent of a theoretical plate. In general, the product of the pressure drop and height equivalent of theoretical plates was reduced as the pulp freeness increased, however. The amount of particulate in the composite material was a significant variable since reducing the amount of particulate in the composite material reduced the weight loss, the pressure drop, and the product of the pressure drop and height equivalent of the theoretical plate. Reducing the amount of particulate produced composite materials with significantly lower capacity factors, lower resolution, and a greater height equivalent of theoretical plates.

An important variable to assess the performance of the composite materials for chromatographic separations is the product of the pressure drop and the height equivalent of a theoretical plate. This product is comparable to the pressure drop per theoretical plate, and a lower value corresponds to a more efficient separation, since at a given flow rate less pressure drop is required to achieve the separation of a theoretical plate. The combination of variables present in run 2 resulted in a significant improvement in the value of the product of a pressure drop and height equivalent of a theoretical plate, when the product was compared to the product of runs 4, 5, 7, and 8, in which either pure Partisil or pure Syloid 620 was used as the particulate. The product of the height equivalent of a theoretical plate and the pressure drop was lower in each run where Partisil was mixed with Syloid 620 than the runs produced with pure Partisil or pure Syloid 620 as the particulate in the composite materials.

TABLE 10

EXPERIMENTAL DESIGN FOR SCREENING DESIGN

| Run number | 1 Particle size ($\mu$) | 2 Silica | 3 Mixture | 4 Amount of refined pulp (%) | 5 Refined Pulp freeness | 6 Amount of[1] particulate % | 7 Dummy |
|---|---|---|---|---|---|---|---|
| 1 | 5 | Partisil | Yes | 6 | −100 | 70 | − |
| 2 | 10 | Partisil | Yes | 4 | −250 | 60 | − |
| 3 | 10 | Syloid 620 | Yes | 4 | −100 | 70 | + |
| 4 | 5 | Syloid 620 | No | 4 | −100 | 60 | − |
| 5 | 10 | Partisil | No | 6 | −100 | 60 | + |
| 6 | 5 | Syloid 620 | Yes | 6 | −250 | 60 | + |
| 7 | 5 | Partisil | No | 4 | −250 | 70 | + |
| 8 | 10 | Syloid 620 | No | 6 | −250 | 70 | − |

[1]Remainder of composite material is unrefined pulp, i.e. long cellulosic fibers.

TABLE 11

COMPOSITION OF MATERIALS IN INITIAL SCREENING DESIGN

| Run number | Syloid 620 (weight %) | Partisil (weight %) | Particle size, ($\mu$) | Amount of refined pulp (%) | Refined Pulp Freeness |
|---|---|---|---|---|---|
| 1 | 35 | 35 | 5 | 6 | −100 |

TABLE 11-continued
COMPOSITION OF MATERIALS IN INITIAL SCREENING DESIGN

| Run number | Syloid 620 (weight %) | Partisil (weight %) | Particle size, (μ) | Amount of refined pulp (%) | Refined Pulp Freeness |
|---|---|---|---|---|---|
| 2 | 30 | 30 | 10 | 4 | −250 |
| 3 | 35 | 35 | 10 | 4 | −100 |
| 4 | 60 | 0 | — | 4 | −100 |
| 5 | 0 | 60 | 10 | 6 | −100 |
| 6 | 30 | 30 | 5 | 6 | −250 |
| 7 | 0 | 70 | 5 | 4 | −250 |
| 8 | 70 | 0 | — | 6 | −250 |

TABLE 12
RESULTS OF THE SCREENING DESIGN I

| Run | Weight loss during sheet formation | Felt formation time (sec) | Ash of composite (%) | Pressure drop (kg/cm² at 6 ml/min) | Resolution at 6 ml/min |
|---|---|---|---|---|---|
| 1 | 11 | 28 | 67 | 16.5 | 4.32 |
| 2 | 11 | 35 | 49 | 7.7 | 3.92 |
| 3 | 16 | 16 | 57 | 11.6 | 4.59 |
| 4 | 9 | 31 | 51 | 14 | 3.23 |
| 5 | 11 | 11 | 50 | 13.7 | 2.91 |
| 6 | 15 | 25 | 49 | 21.7 | 4.46 |
| 7 | 29 | 13 | 52 | 32.2 | 3.73 |
| 8 | 12 | 70 | 66 | 25.2 | 3.73 |

TABLE 13
RESULTS OF THE SCREENING DESIGN II

| Run | H* toluene (.2 ml/min) | H* toluene (6 ml/min) | H* toluene (20 ml/min) | H* DMP (.2 ml/min) | H* DBP (.2 ml/min) |
|---|---|---|---|---|---|
| 1 | 0.758 | 0.482 | 0.610 | 0.922 | 0.904 |
| 2 | 0.606 | 0.746 | 0.802 | 1.120 | 0.964 |
| 3 | 0.580 | 0.331 | 0.431 | 0.930 | 0.833 |
| 4 | 0.756 | 0.921 | 1.050 | 1.450 | 1.240 |
| 5 | 1.060 | 1.940 | 2.170 | 2.790 | 2.040 |
| 6 | 0.611 | 0.332 | 0.451 | 1.320 | 0.790 |
| 7 | 0.778 | 0.600 | 0.726 | 1.700 | 1.240 |
| 8 | 0.711 | 0.518 | 0.712 | 1.900 | 1.070 |

*H in mm

TABLE 14
RESULTS OF THE SCREENING DESIGN III

| Run | H DBP (6 ml/min) | k' DBD (6 ml/min) | H DMP (6 ml/min) | k' DMP (6 ml/min) | H × pressure drop (kg/cm² at 6 ml/min) |
|---|---|---|---|---|---|
| 1 | 0.911 | 1.62 | 1.36 | 4.48 | 22.4 |
| 2 | 1.046 | 1.36 | 1.45 | 3.79 | 11.1 |
| 3 | 0.813 | 1.71 | 1.21 | 4.68 | 14 |
| 4 | 1.453 | 1.43 | 2.00 | 3.75 | 28 |
| 5 | 4.190 | 1.25 | 3.69 | 4.57 | 50.4 |
| 6 | 0.802 | 1.57 | 1.20 | 4.25 | 26 |
| 7 | 1.420 | 1.73 | 2.09 | 5.07 | 67.3 |
| 8 | 1.176 | 1.96 | 1.51 | 4.86 | 38 |

TABLE 15
RESULTS OF THE SCREENING DESIGN IV

| Run | H DBP (20 ml/min) | k' DBD (20 ml/min) | H DMP (20 ml/min) | k' DMP (20 ml/min) | HETP × pressure drop (kg/cm² at 20 ml/min) |
|---|---|---|---|---|---|
| 1 | 1.120 | 1.65 | 1.26 | 4.63 | 79.7 |
| 2 | 1.210 | 1.38 | 1.59 | 3.76 | 42.3 |
| 3 | 0.957 | 1.65 | 1.30 | 4.49 | 55 |
| 4 | 1.770 | 1.45 | 1.86 | 3.81 | 89.8 |
| 5 | 2.880 | 1.32 | 2.97 | 3.16 | 141.4 |
| 6 | 0.938 | 1.64 | 1.16 | 4.40 | 87.7 |
| 7 | 1.610 | 1.68 | 1.90 | 4.95 | 226.2 |
| 8 | 1.480 | 1.95 | 1.61 | 4.79 | 144.3 |

TABLE 16
RESULTS OF THE SCREENING DESIGN V

| Run | DBP, ratio of k' at .2 and 20 ml/min | DMP, ratio of k' at .2 and 20 ml/min | Ratio of the pressure drop at 20 and 6 ml/min |
|---|---|---|---|
| 1 | 1.260 | 1.200 | 3.850 |
| 2 | 1.610 | 1.510 | 3.450 |
| 3 | 1.050 | 1.070 | 3.670 |
| 4 | 1.290 | 1.260 | 3.450 |
| 5 | 1.300 | 1.320 | 3.480 |
| 6 | 1.110 | 1.140 | 3.480 |
| 7 | 2.080 | 1.940 | 3.710 |
| 8 | 0.964 | 0.810 | 3.550 |

TABLE 17
EFFECT OF THE INDEPENDENT VARIABLES ON WEIGHT LOSS DURING SHEET FORMATION

| | Variable | Effect | T-value | Probability |
|---|---|---|---|---|
| 1. | Particle size | 3.50 | 0.83 | 52.90 |
| 2. | Dispersity | 2.50 | 0.59 | 39.20 |
| 3. | Mixture | −2.00 | 0.47 | 31.43 |
| 4. | Amount of pulp | 4.00 | 0.95 | 58.77 |
| 5. | Pulp freeness | −5.00 | 1.18 | 68.70 |
| 6. | Amount of particulate | −5.50 | 1.30 | 72.83 |
| 7. | Dummy | 7.00 | 1.66 | 82.42 |

TABLE 18
EFFECT OF THE INDEPENDENT VARIABLES ON FELT FORMATION TIME (seconds)

| | Variable | Effect | T-value | Probability |
|---|---|---|---|---|
| 1. | Particle size | −8.75 | 0.58 | 38.58 |
| 2. | Dispersity | −13.75 | 0.91 | 57.23 |
| 3. | Mixture | −5.25 | 0.35 | 22.74 |
| 4. | Amount of pulp | −9.75 | 0.65 | 42.71 |
| 5. | Pulp freeness | −14.25 | 0.95 | 58.82 |
| 6. | Amount of particulate | −6.25 | 0.42 | 27.45 |
| 7. | Dummy | −24.75 | 1.64 | 82.18 |

TABLE 19
EFFECT OF THE INDEPENDENT VARIABLES ON PERCENT ASH OF COMPOSITE

| | Variable | Effect | T-value | Probability |
|---|---|---|---|---|
| 1. | Particle size | −0.75 | 0.23 | 14.32 |
| 2. | Dispersity | −1.25 | 0.39 | 25.45 |
| 3. | Mixture | 0.75 | 0.23 | 14.32 |
| 4. | Amount of pulp | −5.75 | 1.78 | 84.96 |
| 5. | Pulp freeness | 2.25 | 0.70 | 45.61 |
| 6. | Amount of particulate | −10.75 | 3.33 | 98.01 |
| 7. | Dummy | −6.25 | 1.93 | 87.64 |

TABLE 20
EFFECT OF THE INDEPENDENT VARIABLES ON PRESSURE DROP (kg/cm² at 6 ml/min)

| | Variable | Effect | T-value | Probability |
|---|---|---|---|---|
| 1. | Particle size | 6.56 | 0.12 | 71.81 |
| 2. | Dispersity | −0.61 | 0.12 | 6.37 |
| 3. | Mixture | −6.91 | 1.34 | 74.02 |
| 4. | Amount of pulp | −2.89 | 0.56 | 37.14 |

TABLE 20-continued
EFFECT OF THE INDEPENDENT VARIABLES ON PRESSURE DROP
(kg/cm² at 6 ml/min)

| Variable | Effect | T-value | Probability |
|---|---|---|---|
| 5. Pulp freeness | 7.79 | 1.51 | 78.88 |
| 6. Amount of particulate | −7.09 | 1.37 | 75.07 |
| 7. Dummy | 3.94 | 0.76 | 49.36 |

TABLE 21
EFFECT OF THE INDEPENDENT VARIABLES ON RESOLUTION AT 6 ml/min

| Variable | Effect | T-value | Probability |
|---|---|---|---|
| 1. Particle size | 0.15 | 0.30 | 19.22 |
| 2. Dispersity | −0.28 | 0.57 | 38.13 |
| 3. Mixture | 0.92 | 1.88 | 86.67 |
| 4. Amount of pulp | 0.01 | 0.03 | 0.90 |
| 5. Pulp freeness | −0.20 | 0.40 | 26.48 |
| 6. Amount of particulate | −0.46 | 0.94 | 58.50 |
| 7. Dummy | 0.12 | 0.25 | 15.54 |

TABLE 22
EFFECT OF THE INDEPENDENT VARIABLES ON H OF TOLUENE AT 0.2 ml/min

| Variable | Effect | T-value | Probability |
|---|---|---|---|
| 1. Particle size | −0.01 | 0.11 | 6.06 |
| 2. Dispersity | 0.14 | 1.15 | 67.33 |
| 3. Mixture | −0.19 | 1.58 | 80.70 |
| 4. Amount of pulp | −0.10 | 0.89 | 55.83 |
| 5. Pulp freeness | 0.11 | 0.94 | 58.68 |
| 6. Amount of particulate | 0.05 | 0.43 | 28.76 |
| 7. Dummy | 0.05 | 0.42 | 27.58 |

TABLE 23
EFFECT OF THE INDEPENDENT VARIABLES ON H OF TOLUENE AT 6 ml/min

| Variable | Effect | T-value | Probability |
|---|---|---|---|
| 1. Particle size | −0.30 | 0.81 | 51.75 |
| 2. Dispersity | 0.42 | 1.12 | 66.27 |
| 3. Mixture | −0.52 | 1.40 | 75.98 |
| 4. Amount of pulp | −0.17 | 0.45 | 30.04 |
| 5. Pulp freeness | 0.37 | 0.99 | 60.93 |
| 6. Amount of particulate | 0.50 | 1.35 | 74.36 |
| 7. Dummy | 0.13 | 0.36 | 23.54 |

TABLE 24
EFFECT OF THE INDEPENDENT VARIABLES ON HETP OF TOLUENE AT 12 ml/min

| Variable | Effect | T-value | Probability |
|---|---|---|---|
| 1. Particle size | −0.32 | 0.79 | 51.11 |
| 2. Dispersity | 0.42 | 1.03 | 62.75 |
| 3. Mixture | −0.59 | 1.47 | 77.86 |
| 4. Amount of pulp | −0.23 | 0.58 | 38.51 |
| 5. Pulp freeness | 0.39 | 0.98 | 60.15 |
| 6. Amount of particulate | 0.50 | 1.24 | 70.74 |
| 7. Dummy | 0.15 | 0.38 | 24.63 |

TABLE 25
EFFECT OF THE INDEPENDENT VARIABLES ON H OF DMP AT 0.2 ml/min

| Variable | Effect | T-value | Probability |
|---|---|---|---|
| 1. Particle size | −0.34 | 0.65 | 42.97 |
| 2. Dispersity | 0.23 | 0.45 | 29.91 |
| 3. Mixture | −0.89 | 1.72 | 83.71 |
| 4. Amount of pulp | −0.43 | 0.84 | 53.42 |
| 5. Pulp freeness | 0.01 | 0.03 | 0.89 |
| 6. Amount of particulate | 0.31 | 0.59 | 39.38 |

TABLE 25-continued
EFFECT OF THE INDEPENDENT VARIABLES ON H OF DMP AT 0.2 ml/min

| Variable | Effect | T-value | Probability |
|---|---|---|---|
| 7. Dummy | 0.34 | 0.65 | 42.97 |

TABLE 26
EFFECT OF THE INDEPENDENT VARIABLES ON H DBP AT 0.2 ml/min

| Variable | Effect | T-value | Probability |
|---|---|---|---|
| 1. Particle size | −0.18 | 0.56 | 36.96 |
| 2. Dispersity | 0.30 | 0.92 | 57.63 |
| 3. Mixture | −0.52 | 1.59 | 80.99 |
| 4. Amount of pulp | −0.13 | 0.40 | 26.37 |
| 5. Pulp freeness | 0.24 | 0.72 | 47.16 |
| 6. Amount of particulate | 0.25 | 0.75 | 48.62 |
| 7. Dummy | 0.18 | 0.55 | 36.57 |

TABLE 27
EFFECT OF THE INDEPENDENT VARIABLES ON H DBP AT 6 ml/min

| Variable | Effect | T-value | Probability |
|---|---|---|---|
| 1. Particle size | −0.66 | 0.77 | 49.89 |
| 2. Dispersity | 0.83 | 0.97 | 59.98 |
| 3. Mixture | −1.17 | 1.37 | 74.86 |
| 4. Amount of pulp | −0.59 | 0.69 | 45.02 |
| 5. Pulp freeness | 0.73 | 0.85 | 54.30 |
| 6. Amount of particulate | 0.79 | 0.93 | 57.89 |
| 7. Dummy | 0.66 | 0.77 | 49.89 |

TABLE 28
EFFECT OF THE INDEPENDENT VARIABLES ON k' DBP AT 6 ml/min

| Variable | Effect | T-value | Probability |
|---|---|---|---|
| 1. Particle size | 0.02 | 0.19 | 11.43 |
| 2. Dispersity | −0.18 | 1.94 | 87.79 |
| 3. Mixture | −0.03 | 0.30 | 19.32 |
| 4. Amount of pulp | −0.04 | 0.47 | 30.92 |
| 5. Pulp freeness | −0.15 | 1.67 | 82.75 |
| 6. Amount of particulate | −0.35 | 3.86 | 99.03 |
| 7. Dummy | −0.03 | 0.30 | 19.32 |

TABLE 29
EFFECT OF THE INDEPENDENT VARIABLES ON HETP × PRESSURE DROP AT 6 ml/min kg/cm²

| Variable | Effect | T-value | Probability |
|---|---|---|---|
| 1. Particle size | 7.53 | 0.44 | 29.38 |
| 2. Dispersity | 11.27 | 0.66 | 43.67 |
| 3. Mixture | −27.55 | 1.62 | 81.67 |
| 4. Amount of pulp | −4.13 | 0.24 | 15.12 |
| 5. Pulp freeness | −6.93 | 0.41 | 26.94 |
| 6. Amount of particulate | −6.55 | 0.39 | 25.34 |
| 7. Dummy | 14.53 | 0.86 | 54.32 |

TABLE 30
EFFECT OF THE INDEPENDENT VARIABLES ON H OF DBP AT 20 ml/min

| Variable | Effect | T-value | Probability |
|---|---|---|---|
| 1. Particle size | −0.27 | 0.53 | 35.13 |
| 2. Dispersity | 0.42 | 0.81 | 52.09 |
| 3. Mixture | −0.88 | 1.71 | 83.48 |
| 4. Amount of pulp | −0.22 | 0.42 | 27.95 |
| 5. Pulp freeness | 0.37 | 0.72 | 47.11 |
| 6. Amount of particulate | 0.41 | 0.79 | 50.95 |
| 7. Dummy | 0.20 | 0.39 | 25.70 |

TABLE 31
EFFECT OF THE INDEPENDENT VARIABLES ON k' OF DMP AT 20 ml/min

| Variable | Effect | T-value | Probability |
|---|---|---|---|
| 1. Particle size | 0.40 | 1.62 | 81.72 |
| 2. Dispersity | −0.25 | 1.01 | 61.75 |
| 3. Mixture | 0.14 | 0.58 | 38.63 |
| 4. Amount of pulp | 0.01 | 0.03 | 1.15 |
| 5. Pulp freeness | −0.45 | 1.85 | 86.22 |
| 6. Amount of particulate | −0.93 | 3.81 | 98.96 |
| 7. Dummy | 0.00 | 0.01 | 0.28 |

TABLE 32
EFFECT OF THE INDEPENDENT VARAIBLES ON H × PRESSURE DROP AT 20 ml/min

| Variable | Effect | T-value | Probability |
|---|---|---|---|
| 1. Particle size | 358.50 | 0.50 | 33.36 |
| 2. Dispersity | 402.50 | 0.56 | 37.41 |
| 3. Mixture | −1,203.50 | 1.68 | 83.04 |
| 4. Amount of pulp | −142.00 | 0.20 | 11.92 |
| 5. Pulp freeness | −480.50 | 0.67 | 44.19 |
| 6. Amount of particulate | −514.00 | 0.72 | 46.93 |
| 7. Dummy | 551.00 | 0.77 | 49.85 |

TABLE 33
EFFECT OF THE INDEPENDENT VARIABLES k' OF DBP AT 20 ml/min

| Variable | Effect | T-value | Probability |
|---|---|---|---|
| 1. Particle size | 0.03 | 0.35 | 22.67 |
| 2. Dispersity | −0.17 | 1.91 | 87.30 |
| 3. Mixture | −0.02 | 0.23 | 14.30 |
| 4. Amount of pulp | −0.10 | 1.16 | 67.83 |
| 5. Pulp freeness | −0.14 | 1.68 | 82.98 |
| 6. Amount of particulate | −0.28 | 3.30 | 97.95 |
| 7. Dummy | −0.04 | 0.41 | 26.78 |

TABLE 34
EFFECT OF THE INDEPENDENT VARIABLES H OF DMP AT 20 ml/min

| Variable | Effect | T-value | Probability |
|---|---|---|---|
| 1. Particle size | −0.32 | 0.66 | 43.72 |
| 2. Dispersity | 0.45 | 0.92 | 57.64 |
| 3. Mixture | −0.76 | 1.56 | 80.23 |
| 4. Amount of pulp | −0.09 | 0.18 | 10.62 |
| 5. Pulp freeness | 0.28 | 0.58 | 38.62 |
| 6. Amount of particulate | 0.38 | 0.78 | 50.22 |
| 7. Dummy | 0.25 | 0.52 | 34.61 |

TABLE 35
EFFECT OF THE INDEPENDENT VARIABLES ON THE DBP RATIO OF k' AT 0.2 AND 20 ml/min

| Variable | Effect | T-value | Probability |
|---|---|---|---|
| 1. Particle size | 0.20 | 1.96 | 73.97 |
| 2. Dispersity | 0.46 | 4.41 | 85.41 |
| 3. Mixture | −0.15 | 1.45 | 69.23 |
| 4. Amount of pulp | 0.35 | 3.36 | 81.83 |
| 5. Pulp freeness | −0.22 | 2.08 | 74.85 |
| 6. Amount of particulate | −0.01 | 0.11 | 31.02 |
| 7. Dummy | 0.10 | 1.00 | 63.21 |

TABLE 36
EFFECT OF THE INDEPENDENT VARIABLES ON THE DMP RATIO OF k' AT 0.2 AND 20 ml/min

| Variable | Effect | T-value | Probability |
|---|---|---|---|
| 1. Particle size | 0.21 | 1.20 | 66.21 |
| 2. Dispersity | 0.42 | 2.45 | 77.34 |
| 3. Mixture | −0.10 | 0.59 | 54.84 |
| 4. Amount of pulp | 0.33 | 1.90 | 73.47 |
| 5. Pulp freeness | −0.14 | 0.80 | 59.54 |
| 6. Amount of particulate | 0.05 | 0.30 | 44.67 |
| 7. Dummy | 0.17 | 1.00 | 63.21 |

TABLE 37
EFFECT OF THE INDEPENDENT VARIABLES ON THE RATIO OF PRESSURE DROP AT 20 and 6 ml/min

| Variable | Effect | T-value | Probability |
|---|---|---|---|
| 1. Particle size | 0.08 | 8.50 | 92.34 |
| 2. Dispersity | 0.09 | 8.50 | 92.34 |
| 3. Mixture | 0.07 | 6.50 | 89.80 |
| 4. Amount of pulp | −0.02 | 2.00 | 74.27 |
| 5. Pulp freeness | 0.07 | 6.50 | 89.80 |
| 6. Amount of particulate | −0.23 | 23.00 | 98.14 |
| 7. Dummy | 0.01 | 1.00 | 63.21 |

TABLE 38
SUMMARY OF THE EFFECTS OF THE INDEPENDENT VARIABLES

| Variable | Change in variable | Composite formation weight loss | Felt drainage time | Pressure drop at 6 ml/min | Resolution | H | Product of pressure drop and H | k' of DBP | k' of DMP |
|---|---|---|---|---|---|---|---|---|---|
| Particle size | − | + | + | + | 0 | − | + | 0 | 0 |
| Partisil present | | 0 | − | 0 | − | + | + | − | 0 |
| Mixture present | | 0 | 0 | − | + | − | − | 0 | − |
| Amount of pulp | − | + | − | 0 | 0 | − | 0 | 0 | − |
| Pulp freeness | + | − | − | − | − | + | − | − | 0 |
| Amount of particulate | − | − | 0 | − | − | + | − | − | − |

NOTE:
+ = positive change.
− = negative change.
0 = no change.

EXAMPLE 7

A column parameter which significantly influences effectiveness of a column to separate components is the amount of axial dispersion. It is convenient to compare the dispersion obtained in different columns by means of a dispersion variance. When the peak eluting is Gaussian, two parameters are needed to establish this curve—the mean and the standard deviation. The variance of the dispersion curve is the square of the standard deviation. The dimensionless variance, obtained by dividing the standard deviation by the mean of the dispersion curve and then squaring the result, can be used to compare the efficiency of various columns.

Following the procedure of Example 4, the dimensionless variances for the chromatographic separation of DMP (dimethyl phthalate) and DBP (dibutyl phthalate) were obtained and are set forth in Table 39. Note that the dispersion for the retained components was not as they did for a column containing 100% particulate. The insensitivity of the composite material with respect to flow rates is an advantage.

TABLE 39

| Flow Rate ml/min | Velocity, V cm/min | Toluene Variance | DBP Variance | DMP Variance | DBP $U/D_{eff}L$ | DMP $U/D_{eff}L$ |
|---|---|---|---|---|---|---|
| Composite | | | | | | |
| 0.2 | 0.06367 | 0.00102 | 0.001291 | 0.001684 | 0.000274 | 0.000667 |
| 0.5 | 0.159 | 0.00113 | 0.00157 | 0.00169 | 0.00044 | 0.000556 |
| 1 | 0.318 | 0.00129 | 0.00179 | 0.00172 | 0.000496 | 0.0004299 |
| 2 | 0.637 | 0.001414 | 0.00193 | 0.00194 | 0.0005118 | 0.000529 |
| 4 | 1.273 | 0.00146 | 0.002086 | 0.00210 | 0.000624 | 0.000643 |
| 6 | 1.91 | 0.00159 | 0.00222 | 0.00216 | 0.000654 | 0.0005977 |
| 8 | 2.55 | 0.00150 | 0.00233 | 0.00216 | 0.000832 | 0.000665 |
| 9.9 | 3.15 | 0.00158 | 0.00279 | 0.00211 | 0.00121 | 0.000535 |
| Silica | | | | | | |
| 1 | 0.318 | — | 0.00544 | 0.000603 | 0.00508 | 0.000311 |
| 2 | 0.637 | 0.000352 | — | — | — | — |
| 6 | 1.91 | 0.000419 | 0.00195 | 0.00133 | 0.00153 | 0.00091 |
| 9.9 | 3.15 | 0.000492 | 0.00224 | 0.00134 | 0.00175 | 0.000848 |
| 12.0 | 3.82 | 0.000571 | 0.00431 | 0.00167 | 0.00374 | 0.00110 |

TABLE 40

| % Syloid 620 | % 250 CSF Pulp | Pressure Drop (kg/cm$^2$) (25 cm) | HETP (mm) DBP | HETP (mm) DMP | k' DEP | k' DMP | Separation Time (min) | Pressure Drop (kg/cm$^2$) (for 99% separation) | Distance (cm) | Total Particulate (gm) |
|---|---|---|---|---|---|---|---|---|---|---|
| 30 | 10 | 35 | 3.014 | 2.972 | 1.1 | 3.0 | 4.00 | 29.3 | 20.2 | 0.90 |
| 50 | 7.5 | 17.2 | 7.453 | 6.672 | 1.0 | 2.8 | 7.55 | 27.8 | 39 | 4.78 |
| 0 | 5 | 26.3 | — | — | — | — | 1.17 | 13.4 | 9.87 | 0.66 |
| 19 | 6 | 31.5 | 1.674 | 1.036 | 0.7 | 1.9 | 3.35 | 12.9 | 7.88 | 1.06 |
| 44 | 6 | 37.8 | 1.85 | 1.343 | 2.9 | 6.6 | | | | |
| 100 | 0 | 27.3 | 0.56 | 0.335 | 3.79 | 9.6 | 1.08 | 20.6 | 1.54 | 0.705 | substantially greater than the dispersion for the non-retained component toluene. Since the dispersion of the retained component depends upon the dispersion due to back mixing in the column itself, any dispersion due to diffusion resistance, the variance due to diffusion or resistance can be obtained by subtracting the toluene variance from the retained component variance. Such calculation is presented in Table 40. Note that most of the column variance is due to longitudinal diffusion or back mixing. The contribution of the diffusional resistance was approximately the same for both DMP and DBP and these results are in contrast to the dispersion obtained with a particulate column of the Syloid 620 which is also presented in Table 40. Relatively sharp peaks were obtained with the unknown retained component toluene and substantially greater dispersion was obtained on the retained components. This indicates that relatively little back mixing or axial diffusion is present in the silica column. There was significant differences in DBP, which is not as highly retained as DMP. At the slower and faster flow rates examined, the diffusional resistance was greater in the particulate column than in the composite column. The contribution due to back mixing will vary depending on the particular composition of a composite column.

EXAMPLE 8

Following the procedure of Example 7, the pressure drops, H, retention factor k' and theoretical minimum column distance required for 99% separation of DMP and DBP were determined and are set forth in Table 40. The pressure drop is approximately linear with flow rate, indicating laminar flow conditions. The dispersion coefficient or amount of back mixing obtained is also apparently linear with flow rate. In general, H for the composite material did not vary as much with flow rate

EXAMPLE 9

The column length needed to achieve a given separation depends on the time of separation between the peaks and peak widths. The time between peaks is a function of the capacity factor, k', and the width between peaks can be expressed as the number of standard deviations (X). The following equation can be used to predict the column length necessary to obtain a specified separation length = (experimental column length) (dimensionless variance) (X)$^2$ [sum of capacity factors plus two/-difference between capacity factors]$^2$.

For the 70% Syloid 620 column described heretofore, 99% of the sample was recovered and the number of standard deviations was 2.33. Accordingly, the column length required for separation of DMP and DBP was only 7 cm. This equation does not take into account column irregularities which may cause channeling and in turn cause peak broadening. Elution curves are also not represented by a normal distribution, particularly at high column loading, which tends to introduce additional error. However, the equation is useful since it permits ease of preliminary design and identification of significant variables for design.

The capacity of a column is related to the time required for a component to elute. Having a high capacity is not necessarily desirable since longer retention times actually lower production capacity if separations are desired. Theoretically the capacity factor is equal to the product of the partition coefficient and the ratio of the exterior surface area of the stationary phase to the volume of the mobile phase. Accordingly, the capacity factor of the stationary phase of the present invention can be adjusted by changing the ratio of the surface area to the void volume of the composite material. The void volume for all of the stationary phases tested, as described in these examples was approximately constant and the fibers demonstrated no separation capacity for the components tested. This suggests that the amount of particulate or particulate mixture in the composite is the major variable which can be used to influence the capacity factor of the composite material. A linear relationship existed between the capacity factor and the ratio of the amount of silica to the void volume.

EXAMPLE 10

FRACTIONATION OF RECOVERED HUMAN PLASMA BY WEAK ANION EXCHANGE MEDIA

A 10 ml aliquot of recovered human plasma diluted tenfold with 0.025 M pH 5.5 sodium acetate buffer (final pH 6.31) was passed through a column conforming to the present invention measuring 12.5 cm high by 2.5 cm i.d. and packed with individual sorption elements containing 70% silica gel (70 micrometer average particle size modified by treatment with 3-amino propyltriethoxy silane). Throughput rate was 5 ml/min. The column was sequentially eluted with (1) 0.025 M sodium acetate buffer pH 6.31,
(2) 0.25 M sodium acetate buffer pH 5.5, 0.25 M sodium acetate buffer pH 4.8 and
(3) 0.25 M sodium acetate buffer pH 4.0.

Figure 11:
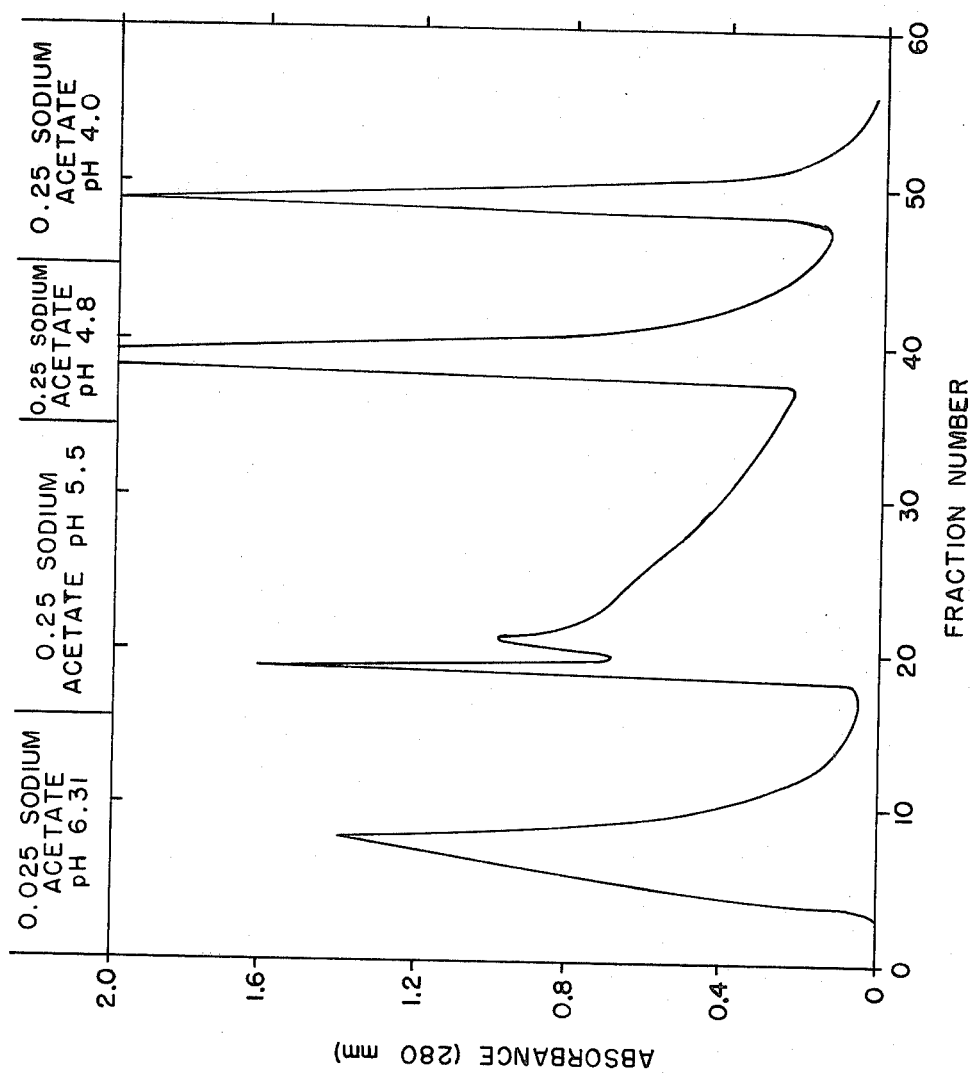

The elution profiles of the four fractions are set forth in FIG. 11. Fractions of approximately 20 ml were collected and twelve were selected to assay for albumin (Sigma No. 630) and globulins (Sigma No. 560). The elution profiles of the twelve fractions are given below in Table 41 and the characteristics of six pooled fractions are given in Table 42.

TABLE 41

| | Elution Profiles of Eleven Selected Fractions | | | | |
|---|---|---|---|---|---|
| Tube Number | O.D. 280 nm | Albumen* (O.D.630) | Globulin** (O.D.560) | Albumen/globulin | Relative Ratio+ |
| Initial | | 0.377 | 0.185 | 2.03 | 1 |
| 4 | 0.45 | 0 | 0.026 | 0 | 0 |
| 7 | 1.22 | 0 | 0.051 | 0 | 0 |
| 11 | 0.27 | 0 | 0.004 | 0 | 0 |
| 18 | 1.60 | 0.17 | 0.029 | 0.59 | 0.29 |
| 20 | 0.90 | 0.054 | 0.040 | 1.35 | 0.67 |
| 22 | 0.75 | 0.026 | 0.019 | 4.52 | 2.23 |
| 24 | 0.66 | 0.103 | 0.010 | 10.30 | 5.07 |
| 30 | 0.41 | 0.080 | 0.006 | 13.33 | 6.57 |
| 38 | >2 | 0.232 | 0.035 | 6.62 | 3.26 |
| 40 | 0.96 | 0.102 | 0.021 | 4.84 | 2.39 |
| 48 | 2.00 | 0.052 | 0.051 | 1.01 | 0.50 |
| 49 | 1.40 | 0.039 | 0.044 | 0.89 | 0.44 |

*Sigma No. 630 Assay
**Sigma No. 560 Assay
+Albumen/globulin ratio of Tube divided by ratio of initial sample.

TABLE 42

| | Characteristics of Six Fooled Fractions | | | |
|---|---|---|---|---|
| Fraction | Tubes | Volume (ml) | Buffer* pH | NaCl (m) |
| I** | 1–11 | 36 | 5.5 | 0 |
| II | 12–20 | 30 | 4.3 | 0 |
| III | 21–32 | 40 | 4.3 | 0.2 |
| IV | 33–50 | 61 | 4.0 | 0.2 |
| V | 51–63 | 44 | 3.8 | 0.2 |
| VI | 64–80 | 57 | 3.8 | 0.5 |

*Buffer = 0.025 M sodium acetate
**Sample application during this fraction

EXAMPLE 11

GLUCOAMYLASE PURIFICATION BY WEAK ANION EXCHANGE MEDIA

A commercial glucoamylase solution was dialyzed against 0.025 M sodium acetate buffer pH 5.5 and filtered through 50 S Zeta Plus cationally modified filter media (AMF Incorporated, White Plains, New York). A 1 ml sample of the solution (45.6 mg/ml protein) was then applied to a chromatographic column (10 cm high and 0.9 cm i.d.) at 1 ml/min (22 PSI) at room temperature. The column was packed with sorption elements of the type described in Example 10. A total of 80 tubes of 3.3 ml fractions were collected and pooled into six fractions corresponding to the different pH and ionic strength step changes in the elution of the proteins (Table 43). The assay results of the six fractions compared to the initial protein sample are given in Table 43 below. These data show that ~77% of the initial activity is recovered in Fraction VI with a 1.8 fold purification.

TABLE 43

| | Protein and Enzyme Activity Results | | | |
|---|---|---|---|---|
| Sample | Protein (mg)* | Enzyme Activity** | Activity/mg | Specific Activity+ |
| Starting | 45.6 | 7.30 | 0.16 | 1 |
| Fraction I | 1.1 | 0 | 0 | 0 |
| Fraction II | 0.6 | 0 | 0 | 0 |
| Fraction III | 1.0 | 0 | 0 | 0 |
| Fraction IV | 11.6 | 0.61 | 0.053 | 0.33 |
| Fraction V | 6.6 | 0.68 | 0.13 | 0.80 |
| Fraction VI | 17.8 | 4.88 | 0.28 | 1.80 |
| Fraction Totals | 38.1 | 6.33 | 0.17 | |

*Lowry assay
**Coupled assay to measure starch hydrolysis to glucose
+Relative to Starting activity per mg

EXAMPLE 12

PURIFICATION OF IMMUNOGLOBULIN G (Ig G)

Each of four chromatographic columns 10 cm high×10 mm i.d. packed with 0.2 g of the sorption element media described in Example 10 were operated at a flow rate of 1.5 ml/min. The Ig G samples (ammonium sulfate fractionation of human serum obtained from Immunoreagents Inc., Sequin, Tex.) were dialyzed against 0.05 M sodium phosphate, pH 6.8 before passage through the column. The columns were eluted with 0.05 M sodium phosphate pH 6.8 and 0.025 M sodium acetate with 0.5 M sodium chloride, pH 4.0.

The results obtained with each column are set forth in the following Table:

TABLE 44

| | | Results of Separation | | | | |
|---|---|---|---|---|---|---|
| COLUMN | SAMPLE | 6.8 RECOVERY | 4.0 RECOVERY | TOTAL RECOVERY | % RECOVERY | % OF TOTAL % RECOVERY IN 6.8 | 6.8/4.0 |
| 1 | 15.5mg | 9.13mg | 2.74mg | 12.915mg | 83% | 70.69% | 3.33 |
| 2 | 32mg | 21.08mg | 6.95mg | 29.66mg | 93.9% | 71.06% | 3.03 |
| 3 | 49.8mg | 33.09mg | 10.7mg | 45.99mg | 92.3% | 71.96% | 3.092 |
| 4 | 65.48mg | 48.41mg | 21.38mg | 62.68mg | 95.7% | 77.23% | 3.9 |

From Table 44 it can be seen that the first three columns yielded similar results. If it is assumed that the separation in the smallest sample was the optimum, it is seen that the distribution of protein (IgG) in the next two samples is very similar with approximately 71% of the recoverable protein eluting with the 6.8 buffer. In the fourth sample, the protein in the 6.8 fraction increased to 77.2% of the recoverable protein, indicating a probable overloading of the column. From this information, the maximum capacity is found to be 25 mg per gram of media.

In order to qualify the purity of the pH 6.8 elution sample, equal amounts of IgG eluant from the 49.8 mg column and the 65.48 mg column were re-chromatographed. Equal amounts from these 6.8 elutants (3B and 4B) were re-chromatographed (3C and 4C). The results of the separation are set forth in the following table:

TABLE 45

| | | Results of Separation of Re-chromatographed Eluants | | | | |
|---|---|---|---|---|---|---|
| SAMPLE | Mg APPLIED | 6.8 ELUTION | 4.0 ELUTION | TOTAL RECOVERY | % TOTAL RECOVERY IN 6.8 | 6.8/4.0 |
| 3A | 49.8mg | 33.09mg | 10.7mg | 45.99mg | 71% | 3.09 |
| 4A | 65.48mg | 48.41mg | 12.38mg | 62.68mg | 77.23% | 3.9 |
| 3B | 16mg | 12.47mg | .779mg | 13.866mg | 89% | 16.01 |
| 4B | 16.1mg | 12.61mg | 1.373mg | 14.617mg | 86.3% | 9.18 |
| 3C | 5.79mg | 4.61mg | .126mg | 4.85mg | 94% | 36.58 |
| 4C | 5.8mg | 4.52mg | .138mg | 4.78mg | 94% | 32.75 |

It can be seen from the elution profiles of 3B and 4B that the 6.8 elution of 3A was purer than that from 4A. In the B series, similar applications yielded different ratios of protein in the 6.8 vs. 4.0 elutions. When the purified IgG samples from the B series were re-chromatographed the elution profiles were almost identical.

EXAMPLE 13
PREPARATIVE SCALE IMMUNOGLOBULIN G (IgG) PURIFICATION

A chromatographic column according to the invention herein (24 cm high×2.5 cm i.d. packed with 33 g of individual sorption elements as described in Example 10) was equilibrated as follows:
500 mls water
200 mls 0.1 M pH 6.8 sodium phosphate
800 mls 0.025 pH 4.0 sodium acetate with 0.5 M sodium chloride
500 mls. 0.1 M pH 6.8 sodium phosphate
1500 mls. 0.05 M pH 6.8 sodium phosphate Equilibration was carried out at 10 mls per minute. The void volume of the column was approximately 80 mls.

Figure 12:
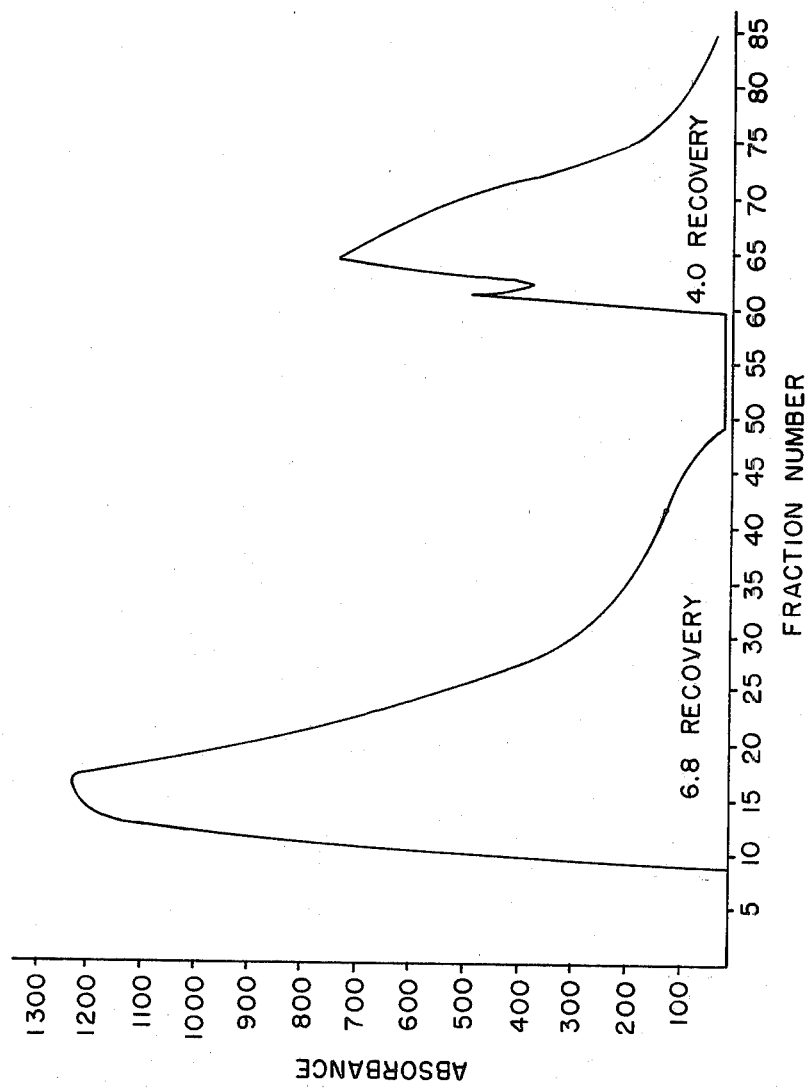

An IgG sample as described in Example 12 was dialyzed against 0.05 M pH 6.8 sodium phosphate before being applied to the column. After dialysis, a 1:100 dilution had an OD 280-0.258 which is equal to 19.1 mg/ml (OD IgG, 1 mg/ml=1.35). 43 mls (821.3 mg) of the IgG solution were passed through the column. Elution was carried out with 0.05 M pH 6.8 sodium phosphate followed by 0.025 M pH 4.0 sodium acetate with 0.5 M sodium chloride. Flow rate was 4 ml per minute. The results of the separation are set forth below and the elution characteristics of the 6.8 and 4.0 recoveries are graphically represented in FIG. 12.

Sample—821.3 mg
6.8 recovery—535.28 mg
4.0 recovery—179.51 mg
Total recovery—724.43 mg
% total recovery—88.48%
% of total in 6.8—73.68%
6.8/4.0—2.98

EXAMPLE 14

In order to compare a column containing the solid stationary phase of this invention with certain prior art columns, in particular U.S. Pat. No. 3,455,818 to Leifield and U.S. Pat. No. 3,856,681 to Huber, which suggest the use of a plurality of sheets of chromatographic media arranged adjacent to each other with the thickness dimension of the layers extending substantially perpendicular to the primary fluid-flow access, a "square" molecular separation column was constructed. The column consisted of a trough 25 millimeters wide, 25 millimeters deep, and 259 millimeters long. A cover was provided which bolted to the trough with an "O" ring to seal the joint. A 0.16 cm hole was drilled into the center of the ends for entrance and exit of the mobile phase. A 0.16 cm thick 25 millimeter square stainless steel frit of 2 μm porosity distributed the solvent at both ends.

The column was packed with sheets consisting of 24% unrefined pulp, 6% of −250 highly refined pulp, and 70% Syloid 620. The material was felted into 30.50 circular sheets. For the vertical packing (prior art) six to eight 25×250 millimeter strips were cut. These were then placed in the column and the cover bolted on. The media was then tested for molecular separation performance. For the horizontal packing, i.e. the substantially homogeneous solid stationary phase of this invention, the same procedure was followed using 25×25 millimeter squares-stacked horizontally along the trough. Both the horizontal strips (invention) and the vertical strips (prior art) were tested in duplicate using a Varian Model 5000 Liquid Chromatograph. In an additional test, both the vertical and horizontal packing were packed as before and then an additional pad or strip added under high pressure to ensure a high packing density in the column.

Samples containing: (1) benzene, (2) beta naphthol, (3) para-nitro-phenol, (4) benzoic acid, and (5) dimethyl phthalate were evaluated. The mobile phase was hexane. The ultraviolet detector used was set at 254 nanometers.

These tests showed that the horizontal packing of the invention gave about an 8 fold increase in column efficiency and much sharper peak shapes indicating much better chromatographic performance than the vertical strips (prior art). This was in spite of the fact that the column was designed and the flow geometry optimized specifically for the vertical strips (prior art). Generally, all of the chromatograms from the injection of the above listed samples showed very "broad" peak shapes and very "bad" tailing for the vertical packing (prior art) when compared to the horizontal packing (invention).

Various changes and modifications can be made in the process and products of this invention without departing from the spirit and scope thereof. The various embodiments which have been described herein were for the purpose of further illustrating the invention, but were not intended to limit it.

We claim:

1. A chromatography column for effecting differential distribution, between two phases, of the components of a sample flowing therethrough, said column containing a solid stationary phase substantially homogeneous with respect to each component thereof, which comprises a porous matrix of fiber having particulate immobilized therein, at least one of said fiber or particulate therein having chromatographic functionality and being effective for chromatographic separation, wherein said solid stationary phase comprises a plurality of sheets of said solid stationary phase elements, the edges of said elements cooperating with the interior wall of the column to form a substantially fluid tight seal therewith, preventing any appreciable skewing or by-pass of fluid around the edges of the elements.

2. The chromatography column of claim 1, wherein the particulate has chromatographic functionality and is effective for chromatographic separation.

3. The chromatography column of claim 2, wherein the fibers are cellulose.

4. The chromatography column of claim 3, wherein the matrix comprises a major amount of long self bonding structural fiber and a minor amount of refined pulp fiber whose Canadian Standard Freeness is in the range of about +100 to −600 ml.

5. The chromatography column of claim 4, wherein the ratio of structural fiber to refined pulp fiber is 2:1 to 10:1.

6. The chromatography column of claim 5, wherein the ratio is 3:1 to 5:1.

7. The chromatography column of claims 1, 2, 3, 4, 5 or 6, wherein the amount of particulate is at least 10 weight percent of said solid stationary phase.

8. The chromatography column of claim 7, wherein the amount of particulate is from 10 to 80 weight percent of said solid stationary phase.

9. The chromatography column of claims 1, 2, 3, 4, 5 or 6, wherein said particulate has a mean particle size of about 5–100 microns.

10. The chromatography column of claim 4, wherein said structural fiber is cellulose having a Canadian Standard Freeness of +400 to +800 ml.

11. The chromatography column of claim 1, 2, 3, 4, 5 or 6, wherein said column is cylindrical and said sheets are discs.

12. The chromatography column of claim 11, wherein said solid stationary phase is hydrophilic swellable.

13. The chromatography column of claim 12, wherein said elements form a fluid-tight seal with the interior wall of the cylinder by water swellable fit therewith.

14. The chromatography column of claim 13, wherein said particulate has a mean particle size of from about 5 to 100 microns and is about 10 to 80 weight percent of said solid stationary phase, said structural fiber is cellulose having a Canadian Standard Freeness of +400 to +800 ml and a ratio of said structural fiber and refined pulp fiber is 3:1–5:1.

15. The chromatography column of claim 1, 2, 3 or 4, wherein said elements form a fluid-tight seal with the interior wall of the cylinder by compression friction fit therewith.

16. In a method of effecting a chromatographic separation by effecting a differential distribution of a sample's components between two phases by passing a mobile phase through a chromatography column containing a solid stationary phase, the improvement which comprises employing as said stationary phase a porous matrix of fiber having particulate immobilized therein, at least one of said fiber or particulate having chromatographic functionality and being effective for chromatographic separation, said solid stationary phase being substantially homogeneous with respect to each component thereof, wherein said solid stationary phase comprises a plurality of sheets of said solid stationary phase elements, the edges of said elements cooperating with the interior wall of the column to form a substantially fluid tight seal therewith, preventing any appreciable skewing or bypass of fluid around the edges of the elements.

17. The method claim 16, wherein the particulate has chromatographic functionality and is effective for chromatographic separation.

18. The method of claim 16, wherein the mobile phase is liquid.

19. The method of claim 17, wherein the fibers are cellulose.

20. The method of claim 19, wherein the matrix comprises a major amount of long self bonding structural fiber and a minor amount of refined pulp fiber whose Canadian Standard Freeness is in the range of about +100 to −600 ml.

21. The method of claim 20, wherein the ratio of structural fiber to refined pulp fiber is 2:1 to 10:1.

22. The method of claim 21, wherein the ratio is 3:1 to 5:1.

23. The method of claims 16, 17, 18, 19 or 20 wherein the amount of particulate is at least 10 percent of said solid stationary phase.

24. The method of claim 23, wherein the amount of particulate is from 10 to 80 weight percent of said solid stationary phase.

25. The method of claims 16, 17, 18, 19 or 20, wherein said particulate has a mean particle size of about 5 to 100 microns.

26. The method of claim 20, wherein said structural fiber is cellulose having a Canadian Standard Freeness of +400 to +800 ml.

27. The method of claim 16, 17, 18, 19, 20, 21 or 22, wherein said column is cylindrical and said sheets are discs.

28. The method of claim 27, wherein said solid stationary phase is hydrophilic swellable.

29. The method of claim 28, wherein said elements form a fluid-tight seal with the interior wall of the cylinder by water swellable fit therewith.

30. The method of claim 29 wherein said particulate has a mean particle size of from about 5 to 100 microns and is about 10 to 80 weight percent of said solid stationary phase, said structural fiber is cellulose having a Canadian Standard Freeness of +400 to +800 ml and the ratio of said structural fiber and refined pulp fiber is 3:1–5:1.

* * * * *